US011957566B2

(12) United States Patent
Bonner et al.

(10) Patent No.: US 11,957,566 B2
(45) Date of Patent: Apr. 16, 2024

(54) IMPLANTS AND METHODS FOR SHOULDER JOINT RECONSTRUCTION

(71) Applicant: B/G Ortho Innovations, LLC, Virginia Beach, VA (US)

(72) Inventors: Kevin Bonner, Virginia Beach, VA (US); Justin W. Griffin, Virginia Beach, VA (US)

(73) Assignee: B/G ORTHO INNOVATIONS, LLC, Virginia Beach, VA (US)

( * ) Notice: Subject to any disclaimer, the term of this patent is extended or adjusted under 35 U.S.C. 154(b) by 299 days.

(21) Appl. No.: 17/175,001

(22) Filed: Feb. 12, 2021

(65) Prior Publication Data
US 2021/0251741 A1 Aug. 19, 2021

Related U.S. Application Data

(60) Provisional application No. 62/976,763, filed on Feb. 14, 2020.

(51) Int. Cl.
*A61F 2/08* (2006.01)
*A61L 27/36* (2006.01)
(Continued)

(52) U.S. Cl.
CPC .......... *A61F 2/0811* (2013.01); *A61L 27/3604* (2013.01); *A61L 27/3662* (2013.01);
(Continued)

(58) Field of Classification Search
CPC .. A61F 2/0811; A61F 2/08; A61F 2/40; A61F 2/30761
See application file for complete search history.

(56) References Cited

U.S. PATENT DOCUMENTS 10,172,703 B2  1/2019 Adams et al.
10,265,160 B2  4/2019 Dooney, Jr. et al.
(Continued)

FOREIGN PATENT DOCUMENTS

WO  WO 2010/127854  11/2010
WO  WO 2019/171181  9/2019

OTHER PUBLICATIONS

Jensen KL. Humeral resurfacing arthroplasty: rationale, indications, technique, and results. Am J Orthop (Belle Mead NJ). Dec. 2007;36(12 Suppl 1):4-8. PMID: 18264550. (Year: 2007).*
(Continued)

*Primary Examiner* — Christie Bahena
*Assistant Examiner* — Cassidy N Stuhlsatz
(74) *Attorney, Agent, or Firm* — Ambrose, Mills & Lazarow, PLLC

(57) ABSTRACT

A method of implanting a graft onto a proximal humerus includes securing a first suture anchor to a first portion of the proximal humerus and securing a second suture anchor to a second portion of the proximal humerus. The first suture anchor includes a first suture and the second suture anchor includes a second suture. The graft is inserted over the proximal humerus. The method further includes positioning the graft relative to the proximal humerus such that a lateral portion of the graft is oriented over a greater tuberosity of the proximal humerus and a medial portion of the graft is oriented over the medial greater tuberosity. The graft is secured to the proximal humerus via the first suture member and the second suture member. The method may also include securing the graft anteriorly to the subscapularis and/or posteriorly to the infraspinatus.

21 Claims, 13 Drawing Sheets

(51) Int. Cl.
*A61B 17/04* (2006.01)
*A61F 2/40* (2006.01)
(52) U.S. Cl.
CPC ... *A61B 17/0401* (2013.01); *A61F 2002/0852* (2013.01); *A61F 2/40* (2013.01); *A61F 2250/0012* (2013.01)

(56) References Cited

U.S. PATENT DOCUMENTS

| | | | |
|---|---|---|---|
| 10,813,742 B2 | 10/2020 | Adams et al. | |
| 2003/0130694 A1* | 7/2003 | Bojarski | A61F 2/0811 606/228 |
| 2007/0191849 A1* | 8/2007 | ElAttrache | A61B 17/0401 606/326 |
| 2008/0027470 A1* | 1/2008 | Hart | A61L 27/54 606/151 |
| 2009/0156997 A1 | 6/2009 | Trenhaile | |
| 2016/0331368 A1* | 11/2016 | Ticker | A61B 17/0401 |
| 2016/0374795 A1* | 12/2016 | Dougherty | A61B 17/0401 606/232 |
| 2017/0143551 A1* | 5/2017 | Coleman | A61B 17/04 |
| 2017/0273680 A1* | 9/2017 | Sengun | A61B 50/30 |
| 2018/0256217 A1 | 9/2018 | Dekel et al. | |
| 2018/0263755 A1* | 9/2018 | Adams | A61B 17/0401 |
| 2019/0091006 A1* | 3/2019 | Adams | A61B 17/0401 |
| 2020/0000573 A1 | 1/2020 | Whittaker et al. | |

OTHER PUBLICATIONS

Laskoviski et al., Arthroscopic rotator cuff re[air with allograft augmentation: making it simple, Jun. 2019, Arthroscopy techniques, vol. 8 Issue 6 (Year: 2019).*
Lenart BA, Ticker JB. Subscapularis tendon tears: Management and arthroscopic repair. EFORT Open Rev. Dec. 15, 2017;2(12):484-495. doi: 10.1302/2058-5241.2.170015. PMID: 29387471; PMCID: PMC5765990. (Year: 2017).*
Mirzayan, Raffy MD, et al. "Failed Dermal Allograft Procedures for Irreparable Rotator Cuff Tears Can Still Improve Pain and Function: The Biologic Tuberoplasty Effect" The Orthopaedic Journal of Sports Medicine, 7(8), 2325967119863432 DOI: 10.1177/2325967119863432, 2019, 7 pages.
Savarese, Eugenio M.D. et al. "New Solution for Massive, Irreparable Rotator Cuff Tears: The Subacromial 'Biodegradable Spacer'" Arthroscopy Techniques, vol. 1, No. 1, Sep. 2012, pp e69-e74.
UW Health Sports Rehabilitation "Rehabilitation Guidelines for Shoulder Arthroplasty and Reverse Ball and Socket Arthroplasty," UW Health Sports Medicine Center, Copyright 2014, 10 pages.
Burnier, Marion MD et al. "Surgical Management of Irreparable Rotator Cuff Tears," The Journal of Bone & Joint Surgery, JBJS.org, vol. 101-A, No. 17, Sep. 4, 2019, pp. 1603-1612.
Mirzayan, Raffy MD, et al. "The Biologic Tuberoplasty Effect in Failed SCR and Bridging Procedures With Dermal Allograft Can Still Improve Pain and Function," 2018 AANA Abstracts, p. e6, SS-14, Apr. 26, 2018, 1 page.

* cited by examiner

IMPLANTS AND METHODS FOR SHOULDER JOINT RECONSTRUCTION

CROSS-REFERENCE TO RELATED APPLICATIONS

This application claims priority to U.S. Provisional Application Ser. No. 62/976,763, entitled "Implants and Methods for Shoulder Joint Reconstruction," filed Feb. 14, 2020, which is incorporated herein by reference in its entirety.

BACKGROUND

The embodiments described herein generally relate to the treatment of large, irreparable, or partially reparable rotator cuff tears in the shoulder. More specifically, the embodiments described herein relate to methods and techniques for improving pain relief, stability, function, and rehabilitated motion.

Rotator cuff tears are a common cause of both pain and disability, especially as patients advance into their 40's, 50's and beyond. For those whom surgery is selected to be the most appropriate option, anatomic repair of the rotator cuff tendon back to the bone utilizing sutures is optimal. Unfortunately, there is a significant subset of patients whose rotator cuff tears are considered "irreparable," meaning the tendon is unable to be anatomically reduced (placed back) to the bone to allow it to heal. This clinical dilemma is not uncommon for patients and shoulder surgeons and are referred to as massive, irreparable rotator cuff tears (MIRCT).

Surgical options for "irreparable" rotator cuff tears are limited, but include partial repair, tendon transfers, superior capsular reconstruction, and shoulder arthroplasty (replacement). Superior capsular reconstruction (also referred to as "SCR") was proposed by Dr. Mihata in Japan as an alternative solution for patients who are not good arthroplasty candidates. In a number of biomechanical and clinical studies utilizing a multi-layered fascia-lata autograft harvested from the hip, Dr. Mihata was able to show improved biomechanics to the glenohumeral joint and clinical outcomes. His technique attempts to reconstruct the superior capsule of the shoulder with inserts on the superior glenoid that spans the greater tuberosity. The rationale for the SCR procedure is that the reconstructed capsule (fixed to both the glenoid and humerus) will keep the humeral head tensioned and depressed into its appropriate position relative to the glenoid. In essence, there is basically a reverse trampoline effect where the graft which is fixed to the glenoid and humerus and the graft does not allow superior migration of the humeral head due to its fixation on both sides of the joint. An important aspect of the SCR procedure is re-establishing the appropriate graft tension when the graft is healed to the glenoid (medial side) and to the greater tuberosity (lateral side). While the SCR implants which heal successfully to the glenoid and greater tuberosity correlate with more positive clinical outcomes, the SCR procedure is challenging and even advanced shoulder surgeons may frequently have difficulty performing the SCR procedure. Unlike Dr. Mihata who pioneered the procedure in Japan utilizing autologous fascia lata from the patients hip, in the United States, most surgeons have opted to utilize an allograft made of human dermis instead of autograft fascia lata in an effort to limit donor site morbidity and surgical time. The SCR procedure, however, even when using an allograft, is technically challenging and takes shoulder surgeons quite a long time to complete. Although some authors have published successful clinical results utilizing a 3 mm dermal allograft, the results of Dr. Mihata have generally not been replicated to date.

Other proposed procedures include placing a biodegradable balloon composed of a copolymer into the subacromial space, and then filling the balloon with saline. Because the balloon is not fixed to the tissues, however, undesirable migration can result. Additionally, the degradation and absorption properties of the balloon can limit the benefit over time. As such, currently there are limited options for addressing pain and mobility for this "irreparable" clinical scenario, especially for physically active patients or younger patients, who are not good candidates for shoulder arthroplasty (replacement). Unfortunately, patients and surgeons are frequently unsatisfied with the above options due to relatively high rates of failure and/or complications.

Thus a need exists for an improved non-arthroplasty implant and technique which provides clinical success in terms of pain relief and improved function while avoiding the problems and technical challenges associated with other available options to treat MIRCT. This is especially true for younger or more active patients who are poor candidates for shoulder arthroplasty. Furthermore, a need exists to develop a new technique that can be performed with proficiency by a full spectrum of orthopedic surgeons who presently struggle with the pitfalls of current options and techniques.

SUMMARY

Implants and methods for shoulder joint reconstruction are described herein. In some embodiments, a method of implanting a graft onto a proximal humerus of a patient includes securing a first suture anchor to a first portion of the proximal humerus and securing a second suture anchor to a second portion of the proximal humerus. The first suture anchor includes a first suture member and the second suture anchor includes a second suture member. The method further includes inserting the graft over the proximal humerus with the graft having a lateral portion and a medial portion. The method further includes positioning the graft relative to the proximal humerus such that the lateral portion is oriented over the most lateral aspect of the greater tuberosity of the proximal humerus and such that the medial portion is oriented over the superior aspect of the humeral head (of the proximal humerus). The method further includes securing the graft to the proximal humerus by tensioning the first suture member and the second suture member.

In some embodiments, the medial portion of the graft may be placed about a footprint of the greater tuberosity. In some embodiments the medial portion of the graft can be placed further medially than the greater tuberosity. For example, in some embodiments the method includes securing the medial portion of the graft to cover a portion of the superior humeral head. In some embodiments, the graft will extend to cover a majority of the greater tuberosity and a portion of the humeral head.

In some embodiments, the securing includes fixing the lateral portion of the graft to the greater tuberosity and fixing the medial portion of the graft to the medial margin of the greater tuberosity or humeral head. In some embodiments, the method includes securing an anterior side portion of the graft to a subscapularis of the patient. In some embodiments, the method includes securing a posterior side portion of the graft to an infraspinatus of the patient.

In some embodiments, the method includes securing a third suture anchor to a third portion of the proximal humerus and securing a fourth suture anchor to a fourth portion of the proximal humerus. In some embodiments, there may also be additional points of fixation of the graft to the bone.

In some embodiments, the graft has a thickness of about 3 mm to 8 mm. In some embodiments, the graft is a biologic implant. The biologic implant can be composed of allograft or autograft tissue. In some embodiments, the graft is a biologic allograft selected from one or more of a quadriceps tendon, achilles tendon, or gluteus medius tendon. In some embodiments, graft is a biologic allograft selected from one or more of a single-layer dermis, a multi-layered dermis, or fascia lata.

In some embodiments, the graft is a synthetic implant configured to cushion the greater tuberosity and superior humeral head.

In some embodiments, the graft is configured to move together with the proximal humerus and to move independently from the acromion and glenoid of the patient.

DETAILED DESCRIPTION

Figure 1:
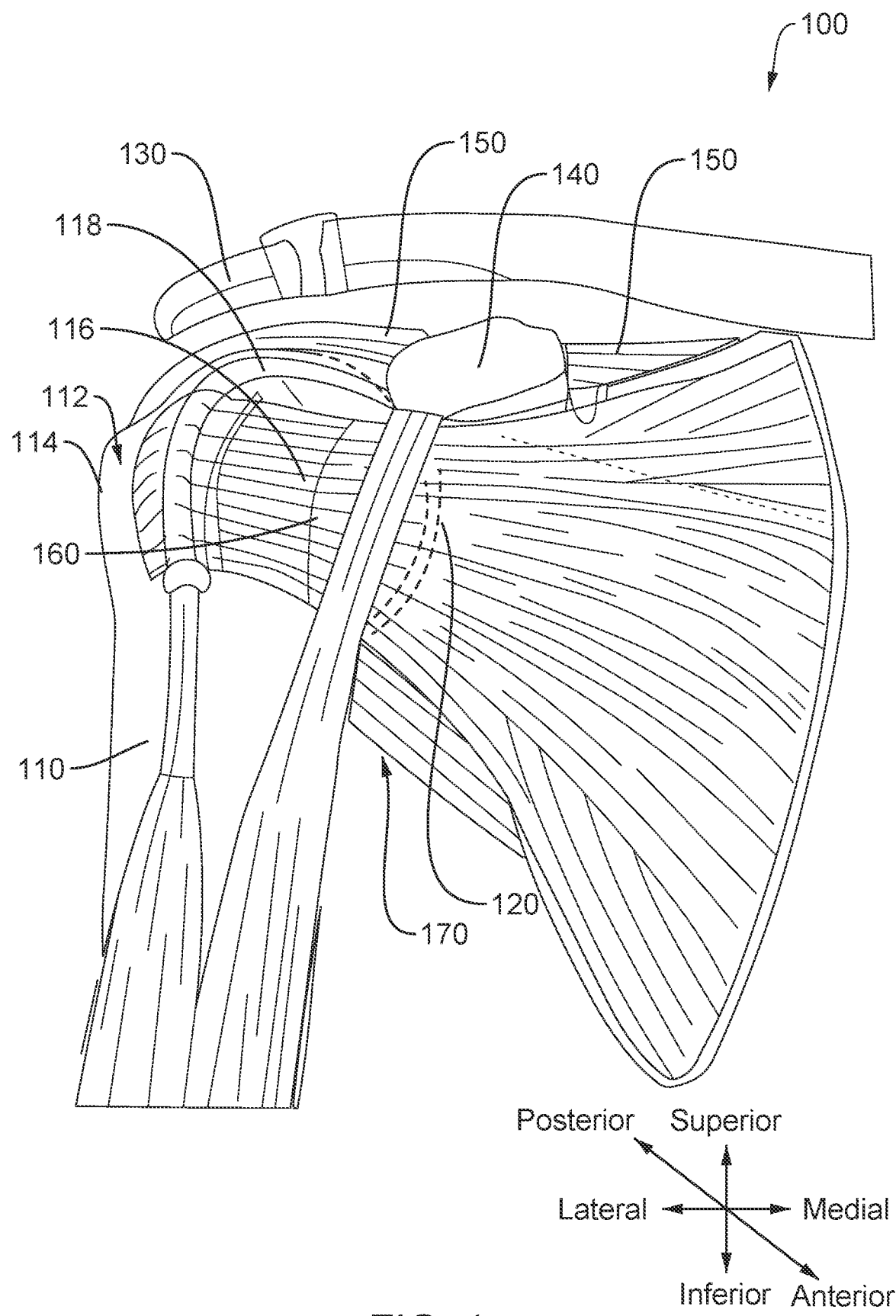
FIG. 1 is a front view of a joint of a human musculoskeletal system.

As discussed above, patients with MIRCT have limited treatment options for addressing pain and improving mobility and function of the shoulder joint. While implants using the SCR procedure have shown some positive clinical outcomes, the difficulty in properly performing the procedure has limited its practical use and adoption. Thus, the methods and embodiments described herein, which include securing an interpositional graft to the humerus without any fixation to the glenoid, may still provide the patient with improved function and alleviate pain. Moreover, the implant and techniques described herein can be performed by a broader spectrum of surgeons on patients classified with an "irreparable" rotator cuff tear to alleviate pain and improve joint function.

The embodiments described herein include positioning an implant (e.g., graft) configured to provide an interpositional cushioning or pillow effect between the greater tuberosity, proximal humerus and the acromion. The interpositional cushioning graft may thus reduce pain, which may allow for improved rehabilitation of the shoulder muscles that are still intact and capable of strengthening with physical therapy. Additionally, the implants placed according to the methods described herein may maintain the humeral head in a lower (i.e., inferior) position, which may provide improved kinematics and help decrease bone-on-bone articulation between the humeral head and acromion. The improved kinematics and reduced likelihood of bone-on-bone contact during articulation in turn helps decrease pain and improve overall function and range of motion of the patient. For patients suffering from rotator cuffs tears, it has further been identified that reducing superior translation and centering of the humeral head onto the glenoid may allow the deltoid and other shoulder muscles to have improved function. While the SCR procedure described above may be capable of repositioning the humeral head in a more optimal anatomic position due to its fixation and proper tensioning on the glenoid and humerus, the difficulty in successfully performing the SCR procedure limits adoption and practical use. Thus, the improved implants and methods for shoulder joint reconstruction, described in greater detail below, provide the benefits of reducing pain and allowing for a more effective rehabilitation of function as pain is reduced without the complex procedures and maneuvers associated with the SCR procedure (e.g., securing anchors to the glenoid and positioning a portion of a graft to extend to the glenoid).

Furthermore, the improved implants and methods described herein do not require attachment or anchoring to the acromion, which is more fragile and susceptible to fracturing and other complications.

In some embodiments, a method of implanting an interpositional graft onto a proximal humerus includes placing one or more medial anchors into a humeral head at a first location medial to a greater tuberosity of the proximal humerus. One or more lateral anchors are placed within the greater tuberosity of the proximal humerus. A medial end portion of the interpositional graft is fixed to the one or more medial anchors and a lateral end portion of the interpositional graft is fixed to the one or more lateral anchors.

In some embodiments, the method includes debriding soft tissue from the greater tuberosity of the proximal humerus. In some embodiments, the method includes decorticating (before the interpositional graft is positioned) a portion of the proximal humerus.

In some embodiments, the method includes fixing an anterior side portion of the interpositional graft to a subscapularis muscle. In some embodiments, the method includes fixing a posterior side portion of the interpositional graft to an infraspinatus muscle.

In the embodiments described herein, the interpositional graft is secured to the humerus and about at least a portion of the greater tuberosity in a manner such that the graft moves together with the proximal humerus and independent of an acromion of the patient. Similarly, the interpositional graft is devoid of a direct securement to the glenoid, and thus graft moves together with the proximal humerus and independent of a glenoid of the patient. The methods described herein are therefore less complex than the SCR procedures referred to above, but also provide for secure placement of an interpositional graft to limit likelihood of migration.

In some embodiments, a kit includes an interpositional graft, a set of medial anchors, and a set of lateral anchors. The interpositional graft is configured to be secured to a proximal humerus, and includes a medial end portion and a lateral end portion. The set of medial anchors is configured to be placed within a humeral head at a first location medial to a greater tuberosity of the proximal humerus. Each of the medial anchors includes at least one of a first suture or a first tape. The set of lateral anchors is configured to be placed within the greater tuberosity of the proximal humerus. Each of the lateral anchors includes at least one of a second suture or a second tape. The medial end portion of the interpositional graft is configured to be coupled to the plurality of medial anchors via the first suture or first tape. The lateral end portion of the interpositional graft is configured to be coupled to the plurality of lateral anchors via the second suture or second tape.

As used in this specification, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

FIG. 1 is a front view of a joint of a human musculoskeletal system 100 including a humerus 110, a glenoid 120, an acromion 130, and a coracoid process 140. The joint further includes rotator cuff muscles and tendons 150, a subscapularis muscle 160, and an infraspinatus muscle 170 (located on a posterior side of the body). The humerus 110 includes a proximal humerus portion 112, a greater tuberosity 114, a lesser tuberosity 116 (which is on the anterior face of the humerus), and a humeral head 118. The glenoid 120 includes a cupped surface for interfacing with a curvature of the humeral head 118.

Figure 2:
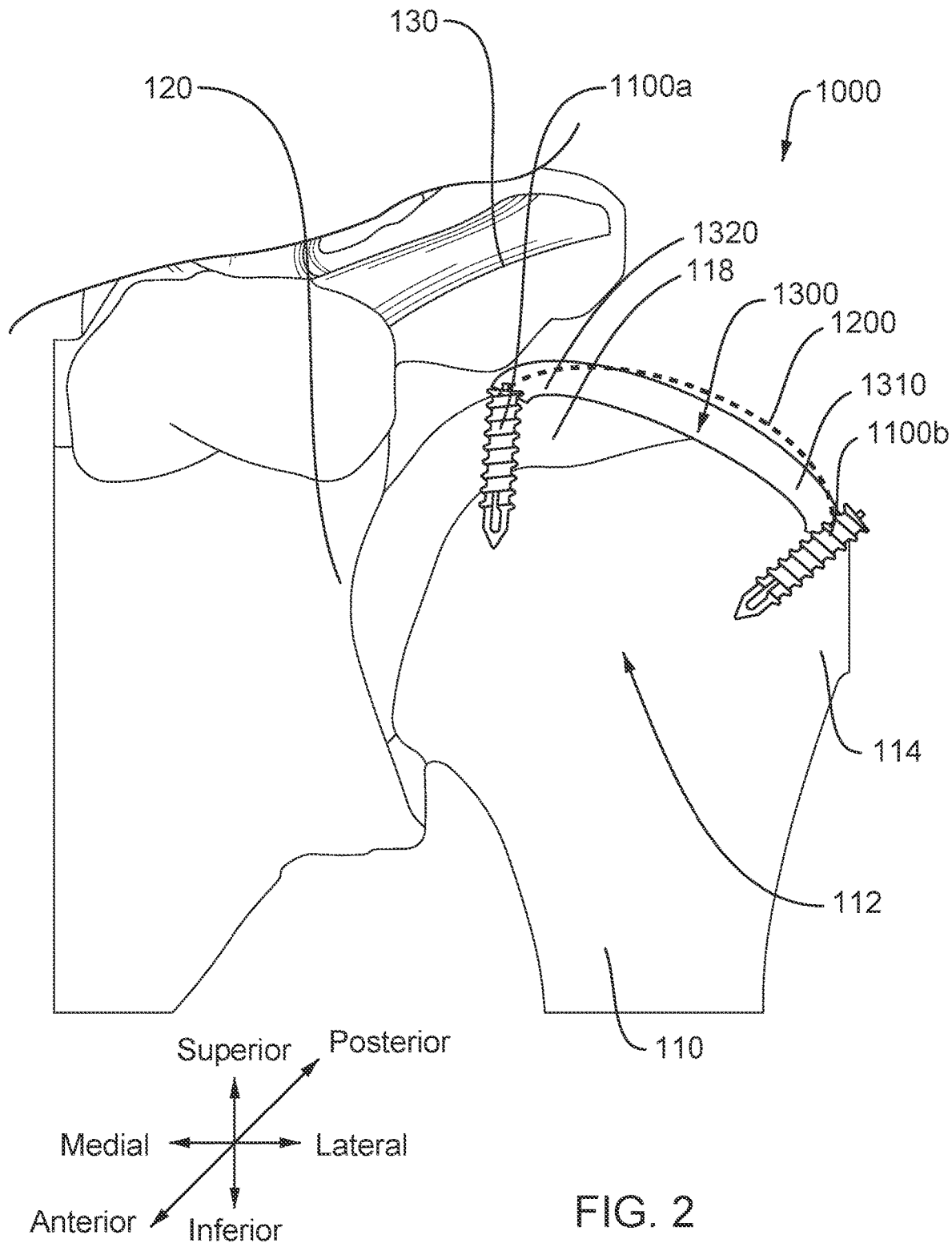
FIG. 2 is a front view of an implant secured to a humerus of the joint using a method according to an embodiment.
Figure 3:
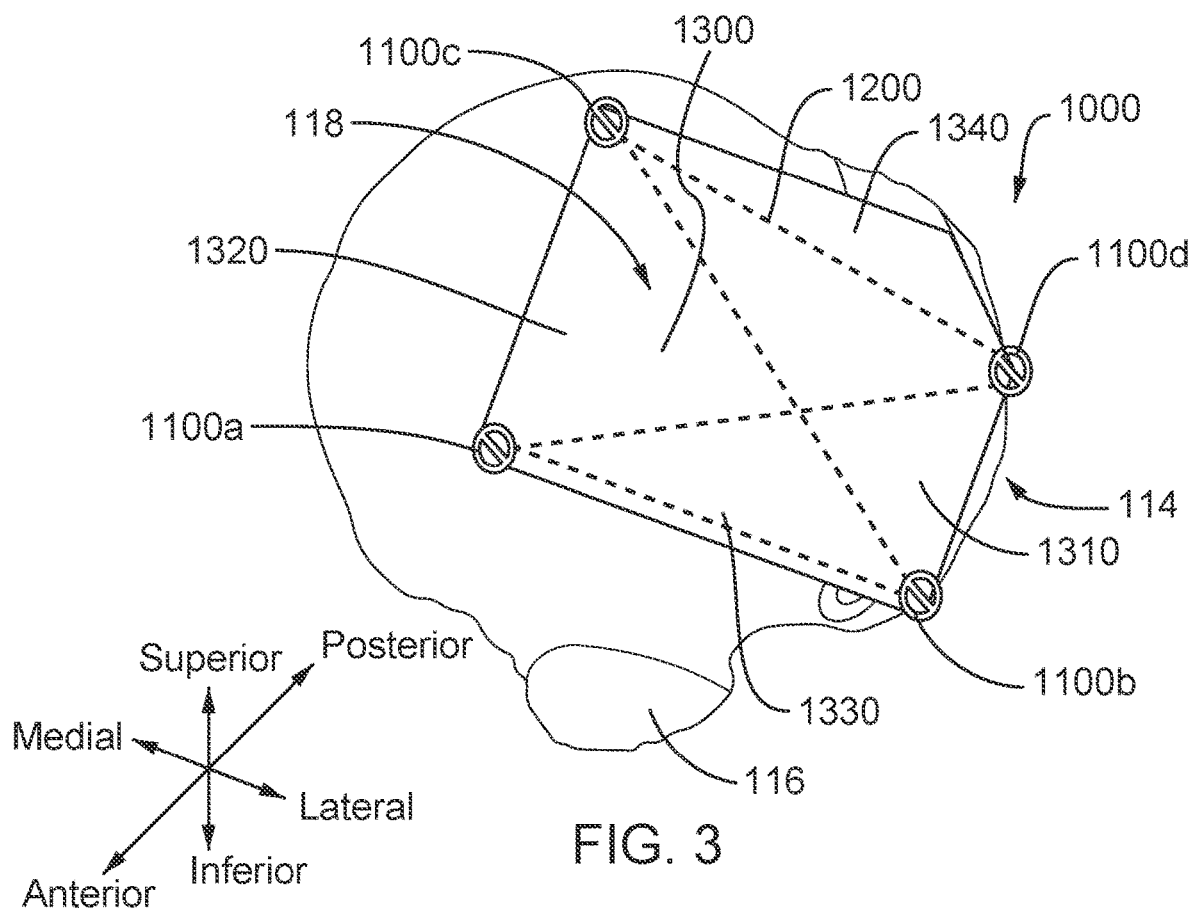
FIG. 3 is a top view of the implant of FIG. 2 secured to the humerus.
Figure 4:
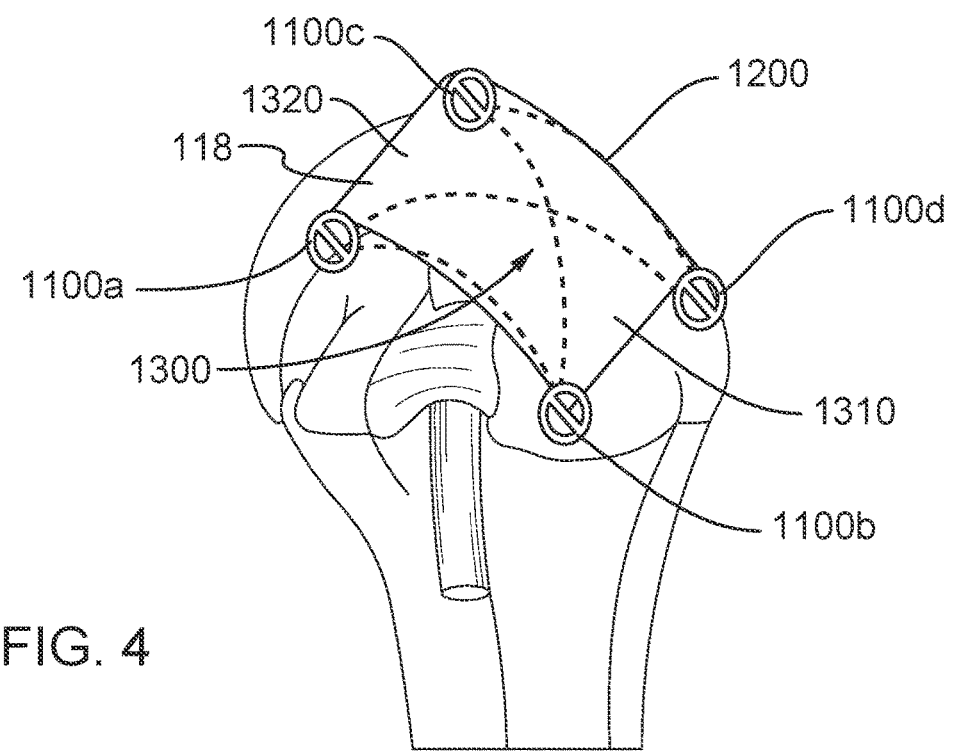
FIG. 4 is a perspective view of the implant of FIG. 2 secured to the humerus.

FIGS. 2-4 show an implant 1000 (also referred to as an implant system or kit) for shoulder joint reconstruction. The implant 1000 includes a graft 1300 that is secured to the humerus 110 using a method according to an embodiment. The implant and associated procedure for securing the implant can be performed when a rotator cuff is deemed to be "irreparable" or in addition to a partial rotator cuff repair procedure. As shown in FIGS. 2-4, the implant 1000 is secured exclusively on a proximal humerus portion 112. Similarly stated, as described in more detail herein, the only bone structure to which the implant 1000 is secured is the humerus and thus the graft functions as an interpositional graft without any medial attachment to the glenoid 120. In some embodiments, a set of suture anchors 1100a, 1110b is secured to the proximal humerus portion 112 and a graft 1300 is secured to the proximal humerus portion 112 via suture members 1200 of suture anchors 1100a, 1100b. The method for securing the graft 1300 to the humerus 110 (and any of the methods described herein) can be performed arthroscopically or by open surgery.

The graft 1300 includes a lateral portion 1310, a medial portion 1320, an anterior side portion 1330, and a posterior side portion 1340. Although shown generally with a rectangular perimeter, the graft 1300 may have any shape suitable based on space constraints within the joint 100 (e.g., the size and shape of the graft may be tailored based on a patient's individual size and anatomy), the desired amount of humeral surface to be covered, and/or size available from harvest location. The graft 1300 and any of the grafts described herein may be a biologic implant or a non-biologic device. In some embodiments, the graft 1300 (or any of the grafts described herein) is a biological allograft, autograft, or xenograft. The biologic allograft may be selected from one or more of a quadricep tendon, a single or multi-layered dermis, an achilles tendon, or gluteus medius tendon. In some embodiments, the biologic allograft may be a single-layer dermis, or multi-layered dermis or fascia lata. In some embodiments, the non-biologic (or synthetic) graft is constructed from silicon (e.g., a silicon implant) or other suitable biocompatible materials. Depending on the patient and application, a thicker graft may minimize superior humeral head translation to promote centering of the humeral head onto the glenoid thereby improving kinematics, pain management, and joint function, as will be appreciated by one skilled in the art. In some embodiments, a thickness of the graft 1300 (or any of the grafts described herein) can be between about 3 mm to 10 mm. In some embodiments, a thickness of the graft 1300 (or any of the grafts described herein) is between about 4 mm to 6 mm. In some embodiments, the thickness of the graft 1300 (or any of the grafts described herein) is between about 6 mm to 9 mm. In some embodiments, the thickness of the graft 1300 (or any of the grafts described herein) is about 8 mm. To accommodate the desired thickness, in some embodiments, the graft 1300 (or any of the grafts described herein) can be formed from a tendon (as described herein). In some embodiments, the graft can be formed from a thicker single or multi-layered dermis (greater or equal to 3 mm thick).

In some embodiments, a first suture anchor 1100*a* is secured to a first (e.g., medial) portion of the proximal humerus portion 112 and the second suture anchor 1100*b* is secured to a second (e.g., lateral) portion of the proximal humerus portion 112. In some embodiments, the first portion of the proximal humerus portion 112 is the humeral head 118 and the second portion of the proximal humerus portion is the greater tuberosity 114. In some embodiments, the first portion is a superior portion of the humeral head 118.

Referring to FIG. 3, in some embodiments, the implant 1000 can be secured to the humerus via a third suture anchor 1100*c* secured to a third portion of the proximal humerus portion 112 and a fourth suture anchor 1100*d* secured to fourth portion of the proximal humerus portion 112. The third portion of the proximal humerus portion 112 is the humeral head 118 and the fourth portion of the proximal humerus portion is the greater tuberosity 114. In some embodiments, the first third suture anchors 1100*a*, 1100*c* (e.g., lateral row of anchors) are secured to the humeral head 118 prior to the second and fourth suture anchor 1100*b*, 1100*d* (e.g., medial row of anchors) being secured to the greater tuberosity 114. In some embodiments, the second and fourth suture anchors 1100*b*, 1100*d* are secured to the greater tuberosity 114 after the graft 1300 has been delivered and positioned over the proximal humerus portion 112. In some embodiments, the second and fourth suture anchors 1100*b*, 1100*d* are secured after to the greater tuberosity 114 prior to or together with the delivery and positioning of the graft 1300.

In some embodiments, the medial portion 1320 of the graft 1300 is fixed to humeral head 118 via at least one of the first suture anchor 1100*a* and the third suture anchor 1100*c*. In some embodiments, the lateral portion 1310 of the graft 1300 is fixed to the greater tuberosity 114 via at least one of the second suture anchor 1100*b* and the fourth suture anchor 1100*d*. In some cases, a patient may further benefit from having the graft 1300 being secured to one or both the anterior and the posterior rotator cuff tissue. In some embodiments, the anterior side portion 1330 of the graft 1300 is secured to a subscapularis muscle 160 of the patient via the suture members 1200. In some embodiments, the graft 1300 can include an anterior "cuff" of graft (i.e., excess graft) to allow suturing of the graft 1300 to the subscapularis tissue. In some embodiments, the graft 1300 can include a medial cuff that extends medial beyond one or more of the first suture anchor 1100*a* and the third suture anchor 1100*c*. In some embodiments, the posterior side portion 1340 of the graft 1300 is secured to the infraspinatus muscle 170 of the patient via the suture members 1200. In some embodiments, the graft 1300 can include a posterior cuff to allow suturing of the graft 1300 to the infraspinatus muscle 170.

In some embodiments, a portion of the perimeter of the graft 1300, including the lateral portion 1310 and the medial portion 1320, is secured to the humerus 110. By maintaining substantially the full length (i.e., lateral to medial) of the graft 1300 secured to the humerus, healing of the graft to the humerus can be facilitated. In some embodiments, substantially the entire perimeter (including the anterior side portion 1330 and the posterior side portion 1340) can be secured to the humerus. In some embodiments, an entire medial portion 1320 of the graft 1300 is secured to a superior portion of the humeral head 118. In some embodiments, an entire lateral portion 1310 is secured to the greater tuberosity 114. In some embodiments, anterior and/or posterior portions of the graft 1300 may further be fixed to existing rotator cuff muscles (e.g., subscapularis and infraspinatus).

Once the graft 1300 is fixed to the proximal humerus portion 112, the graft 1300 moves together with the humerus and independent of either the glenoid 120 or the acromion 130. Thus, by being devoid of any attachment to the glenoid 120, the graft 1300 does not produce any tension on the humerus 110, and instead functions as an interpositional graft in the subacromial space. Moreover, because the graft 1300 is secured to the humerus 110, the graft 1300 will not migrate within the subacromial space over time. Additionally, because there is no stress or tension on the graft from being fixed to the glenoid, an optimal healing environment is provided for the graft to heal to the proximal humerus (greater tuberosity and medial to the tuberosity on the superior humeral head). This tensionless repair enables a more aggressive post-operative therapy program compared to both standard rotator cuff repair and SCR rehabilitation protocols.

Figure 5:
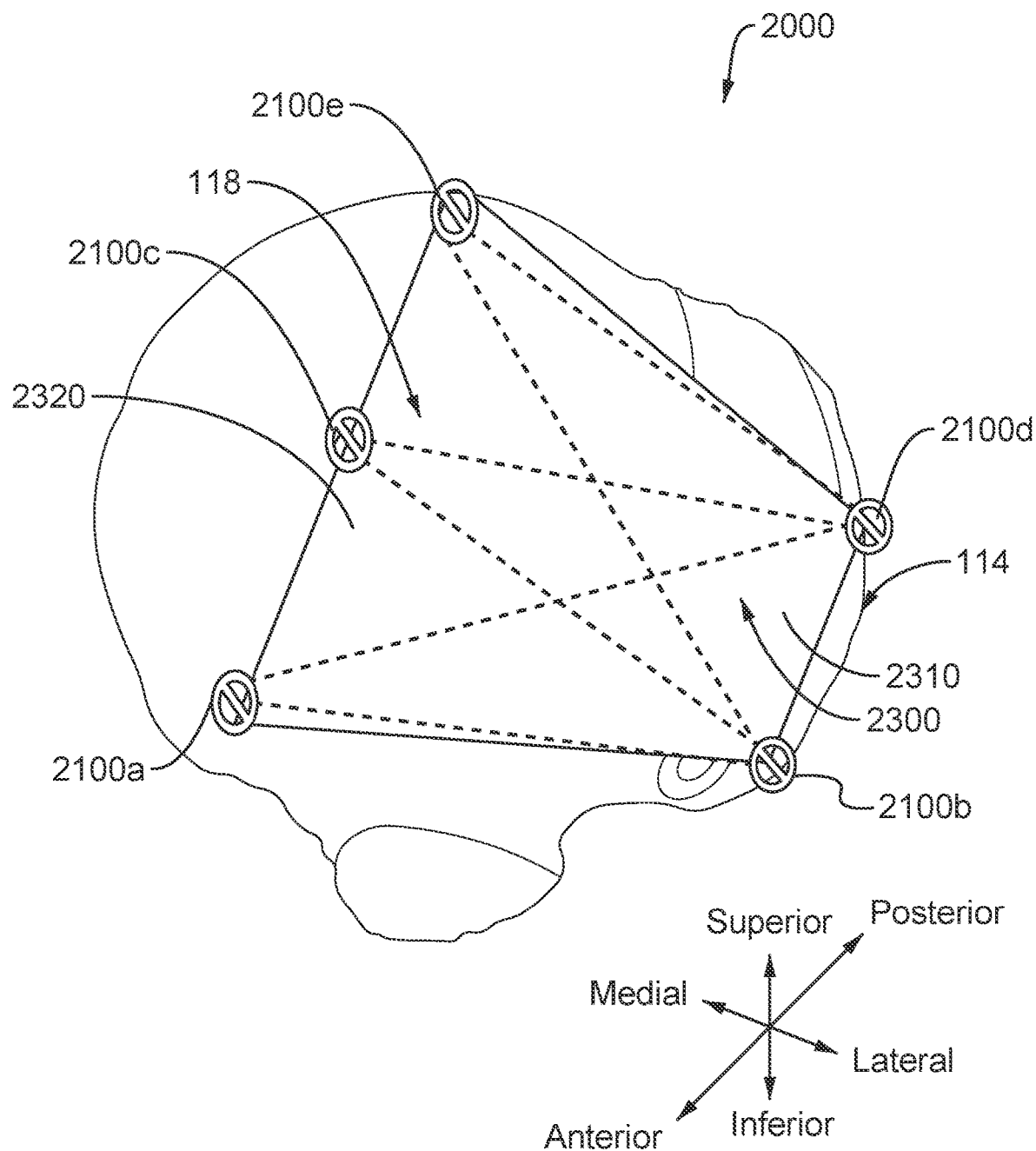
FIG. 5 is a top view of an implant secured to a humerus of the joint using a method according to an embodiment.

Although shown as including four suture anchors (placed in a medial row and a lateral row), in other embodiments, a method can employ any suitable number of suture anchors to secure the graft to the humerus. With reference to FIG. 5, an implant (or implant system or kit) 2000 according to an embodiment is shown. Similar to the implant 1000 of FIGS. 2-4, the implant 2000 includes a graft 2300 (which includes a lateral portion 2310 and a medial portion 2320) secured to the proximal humerus portion 112 with a set of suture anchors 2100*a*, 2100*b*, 2100*c*, 2100*d*, 2100*e*. Unlike the implant 1000 of FIGS. 2-4, the graft 2300 is a trapezoidal shape, and the implant 2000 further includes a fifth suture anchor 2100*e* secured to a fifth portion of the proximal humerus portion 112. The fifth portion of the proximal humerus portion is the humeral head 118. As shown in FIG. 5, the third suture anchor 2100*c* is offset in a posterior direction relative to the first suture anchor 2100*a*. The fourth suture anchor 2100*d* is offset in a posterior direction relative to the second suture anchor 2100*b*. The fifth suture anchor 2100*e* is offset in a posterior direction relative to the fourth suture anchor 2100*d*. In general, the first, third, and fifth suture anchors 2100*a*, 2100*c*, 2100*e* form a first row of anchors (i.e., a medial row), and the second and fourth suture anchors 2100*b*, 2100*d* form a second row of anchors (i.e., a lateral row). The dual row of anchors enable the graft 2300 to be fixed to the proximal humerus portion 112 in a more simplistic, expeditious and cost-effective manner. Although five suture anchors 2100*a*-2100*e* are shown, it will be appreciated by one skilled in the art that a different number of anchors and/or arrangement of suture anchors can be employed for a specific patient or scenario. Furthermore, although the first row is shown as being arranged in generally a linear configuration, the first row may also be arranged in a curvilinear arrangement to follow a contour and/or perimeter of the humeral head 118. For example, the number of suture anchors selected can be between 2 to 9.

Figure 6:
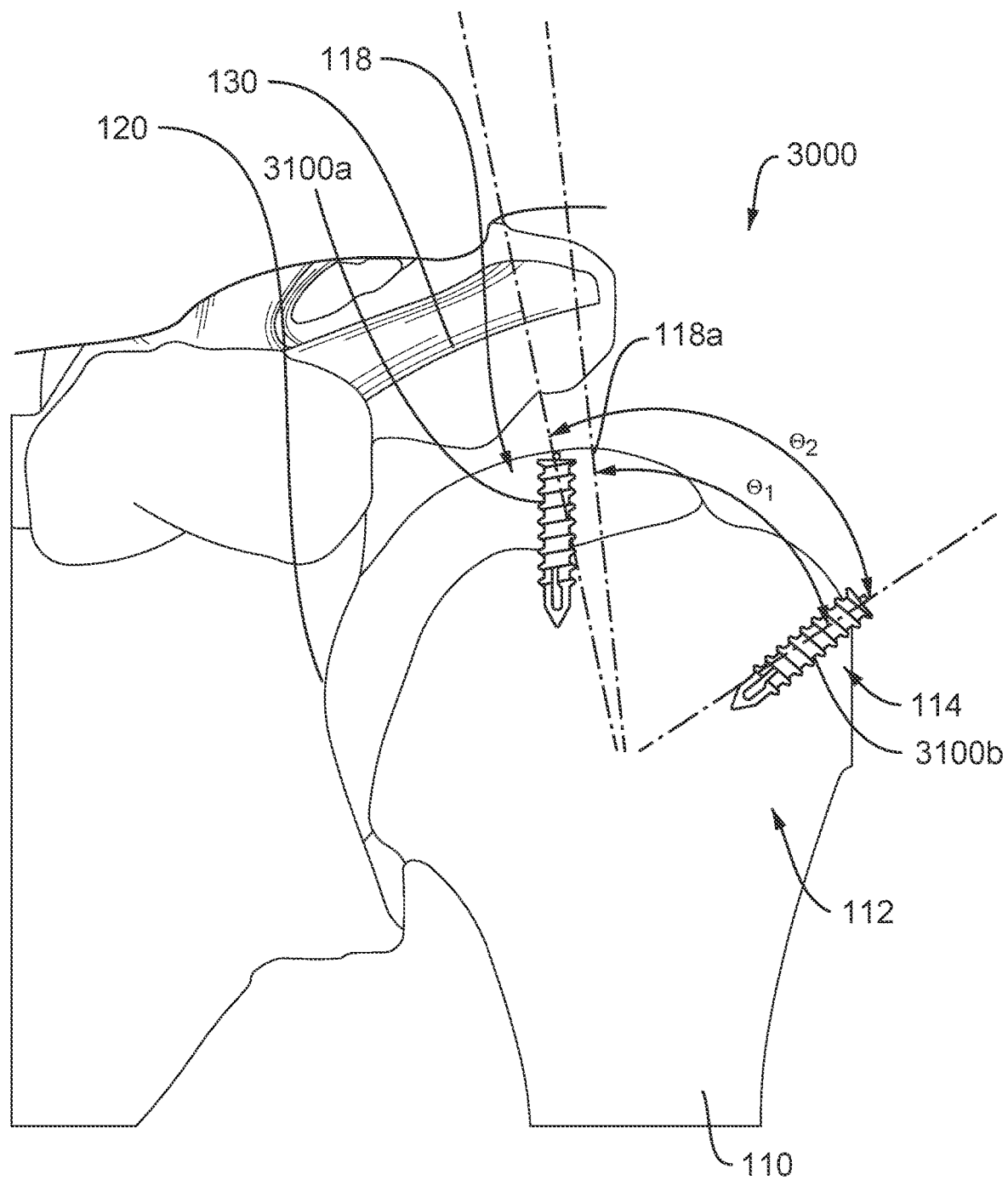
FIG. 6 is a front view of a humerus having suture anchors placed using a method according to an embodiment.

The grafts (and methods) described herein can cover any suitable portion of the proximal humerus. For example, FIG. 6 shows an implant anchor configuration 3000 according to an embodiment. As described herein, a set of suture anchors (e.g., 1100*a*-1100*d*, 2100*a*-2100*e*) can be placed within the humerus to secure a corresponding graft 1300, 2300. Referring to FIG. 6, in some embodiments, a first row of suture anchors 3100a (e.g., medial anchors) can be fixed to the humeral head 118 and a second row of suture anchors 3100b (e.g., lateral anchors) can be fixed to a greater tuberosity 114. Although two rows of suture anchors are shown and described, it will be appreciated by one skilled in the art that additional rows of suture anchors can be utilized, or alternatively, the suture anchors can be arranged to generally follow an outer perimeter of a selected graft. Moreover, although the second row of suture anchors 3100b is shown as being placed within the greater tuberosity 114, in other embodiments, a lateral row of anchors can be placed inferior of (i.e., slightly below) the greater tuberosity.

The first row of suture anchors 3100a is offset from the second row of suture anchors 3100b to facilitate the graft (not shown in FIG. 6) covering the desired portion of the humerus. In some embodiments, the first row of suture anchors 3100a is fixed to a superior portion 118a of the humeral head 118. In this manner, the attachment point produced by the first row of suture anchors 3100a can form a graft angle Θ1 with the attachment point produced by the second row of suture anchors 3100b. The graft angle Θ1 (which can be defined from a center point of the proximal humerus) can provide an indication of how much of the outer surface of the proximal humerus is covered by the graft and/or attachment distance between the lateral end portion of the graft and the medial end portion of the graft. For example, when the first row of suture anchors 3100a and the second row of suture anchors 3100b are positioned to produce a larger graft angle, the graft will cover and/or be secured to a greater portion of the proximal humerus than would occur for a smaller graft angle. In some embodiments, the first row of suture anchors 3100a can be fixed to the superior portion of the humeral head at a more medial location, as shown by the graft angle Θ2. The graft angles Θ1 and Θ2 can be any suitable values, for example, greater than 45 degrees, greater than 75 degrees, greater than about 85 degrees, between about 75 degrees and about 105 degrees, or any suitable value therein. Similarly stated, in some embodiments, the first row of suture anchors 3100a is fixed at about an eleven o'clock position relative to a top of the superior portion 118a. However, it is contemplated that the first row of suture anchors 3100a can be fixed between about the eleven o'clock to one o'clock positions relative to the top of the superior portion 118a. In some embodiments, the second row of suture anchors 3100b can be fixed to the greater tuberosity 114 between about the one o'clock to three o'clock positions relative to the top of superior portion 118.

Figure 7:
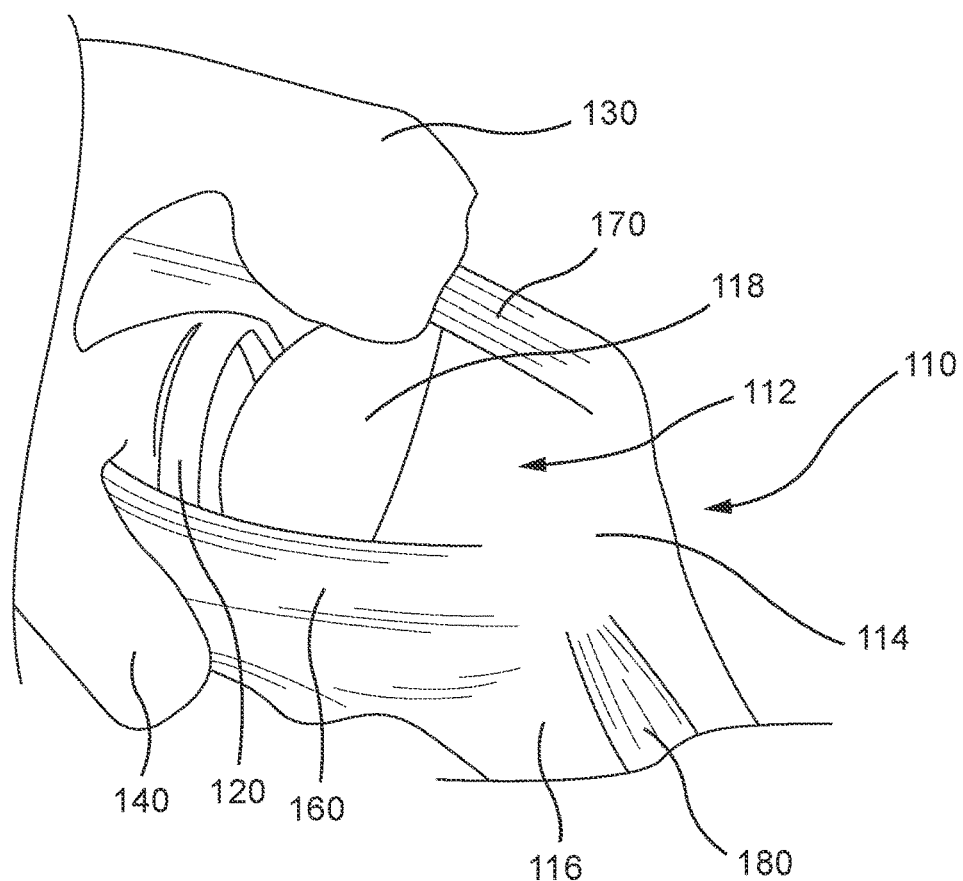
FIG. 7 is a perspective view of a shoulder joint of a patient.

FIG. 7 is a perspective view of the shoulder joint 100 of a patient including the humerus 110, the glenoid 120, the acromion 130, the coracoid process 140. The humerus 110 includes the proximal humerus portion 112, the greater tuberosity 114, the lesser tuberosity 116, and the humeral head 118. As shown in FIG. 7, the joint 100 further includes the subscapularis muscle 160 and the infraspinatus muscle 170. A biceps brachii (long head) 180 is attached to the proximal humerus portion 112.

Figure 8:
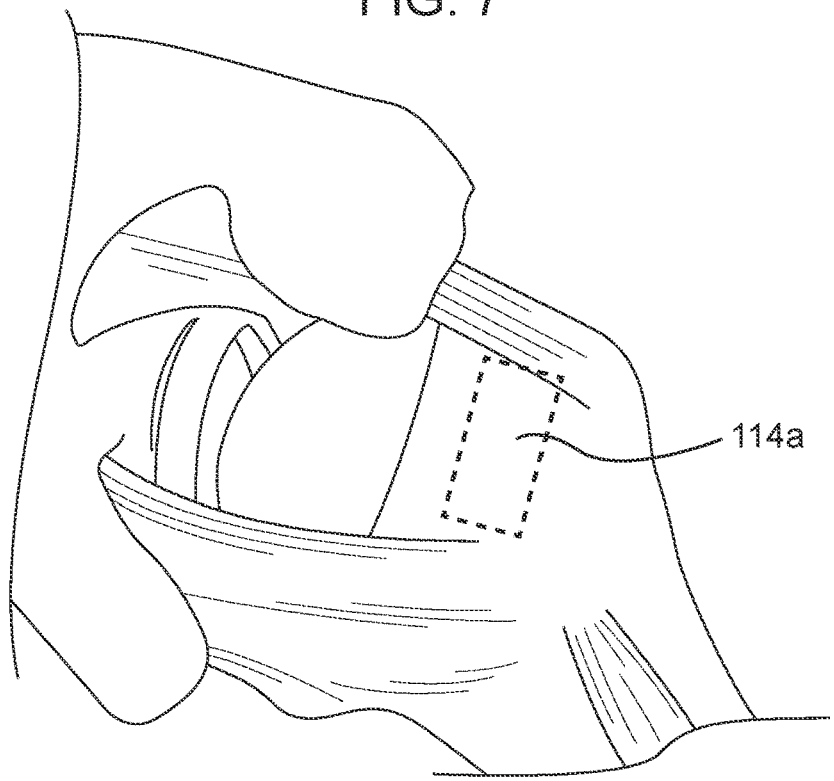
FIGS. 8-9 are perspective views of the shoulder joint of FIG. 7 being prepared using a method according to an embodiment.

FIGS. 8-16 generally depict shoulder joint reconstruction techniques in accordance with aspects of the present disclosure. In some embodiments, a method of shoulder joint reconstruction includes debriding soft tissue from the greater tuberosity 114 where the rotator cuff is torn and no longer attached. In some embodiments, as shown in FIG. 8, the method includes abrading and decorticating the greater tuberosity 114 to provide an optimal healing footprint 114a on the proximal humerus portion 112.

Figure 9:
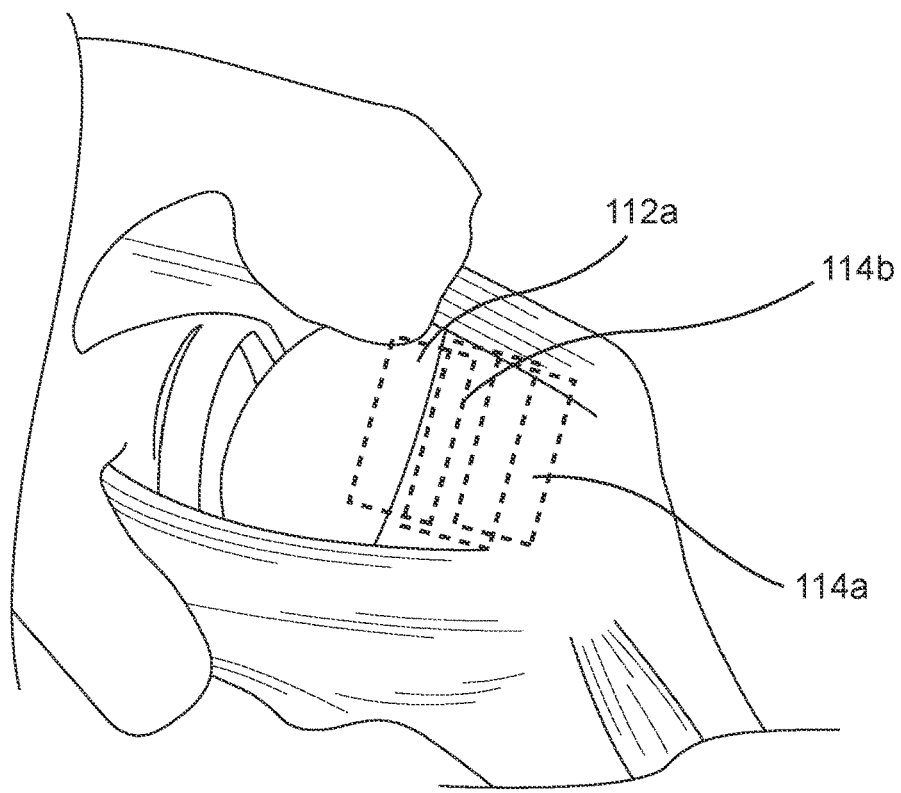

In some embodiments, as shown in FIG. 9, the method includes abrading and decorticating the proximal humerus portion 112a medial to the tuberosity footprint 114b onto an articular cartilage of a superiorlateral portion of the humeral head 118. In some embodiments, the abrading and decorticating is performed up to a superior aspect of the humeral head. Some variability may exist from patient to patient in preparing an area medial to the tuberosity based on anatomy and desirability to fix anchors into a superior portion of the humeral head as described herein. In some embodiments, a spinal needle (not shown) can be used to determine ideal locations for deploying anchors into the humeral head 118 medial to the tuberosity. In some embodiments, the abrading and decorticating is performed up to a location lateral to where anchors (e.g., medial) are deployed into the humeral head 118.

Figure 10:
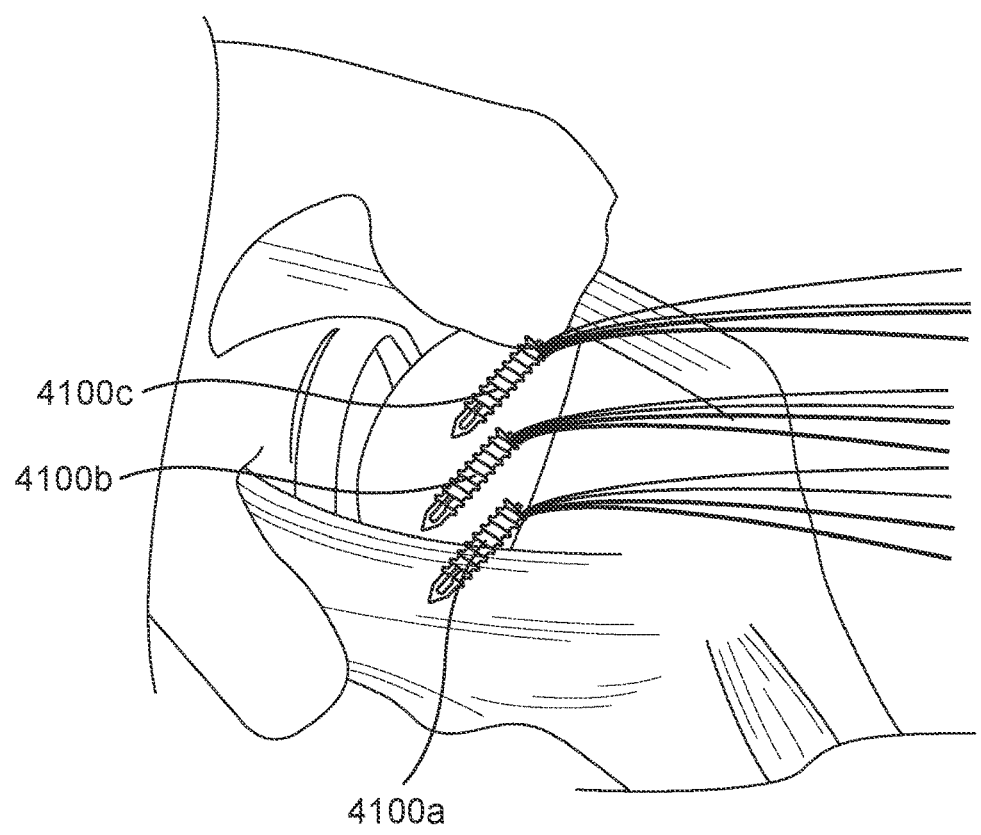
FIG. 10 is a perspective view of the shoulder joint of FIG. 9 with anchors fixed to the humeral head using a method according to an embodiment.

In some embodiments, as shown in FIG. 10, one or more medial anchors 4100a, 4100b, 4100c are mounted to the humeral head 118 at a location between the tuberosity and the superior humeral head. In some embodiments a minimum of two medial anchors 4100a, 4100b are mounted to the humeral head 118. In some embodiments, three anchors 4100a, 4100b, 4100c are mounted to the humeral head 118 to optimize graft fixation to the bone. In some embodiments, four anchors (not shown) are mounted to the humeral head 118 to further optimize graft fixation to the bone.

Figure 11:
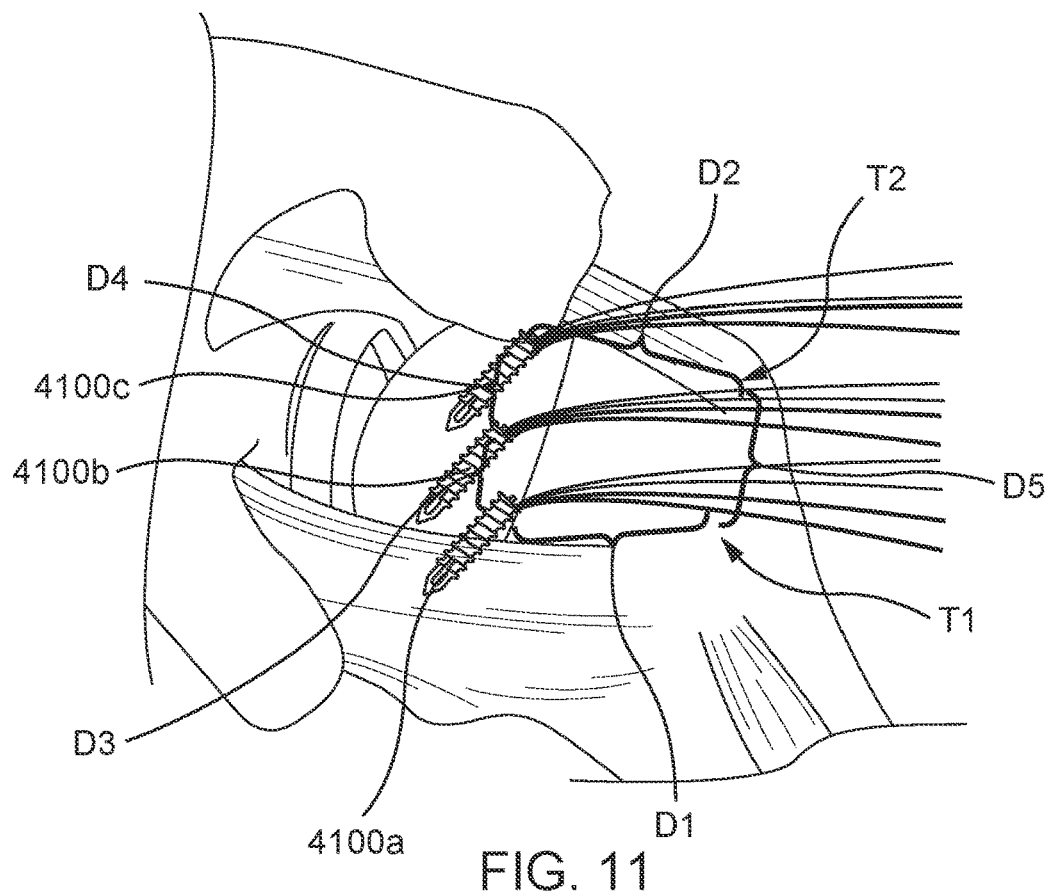
FIG. 11 is a perspective view of the shoulder joint of FIG. 10 with anchors fixed to the humeral head being prepared for implant delivery using a method according to an embodiment.
Figure 12:
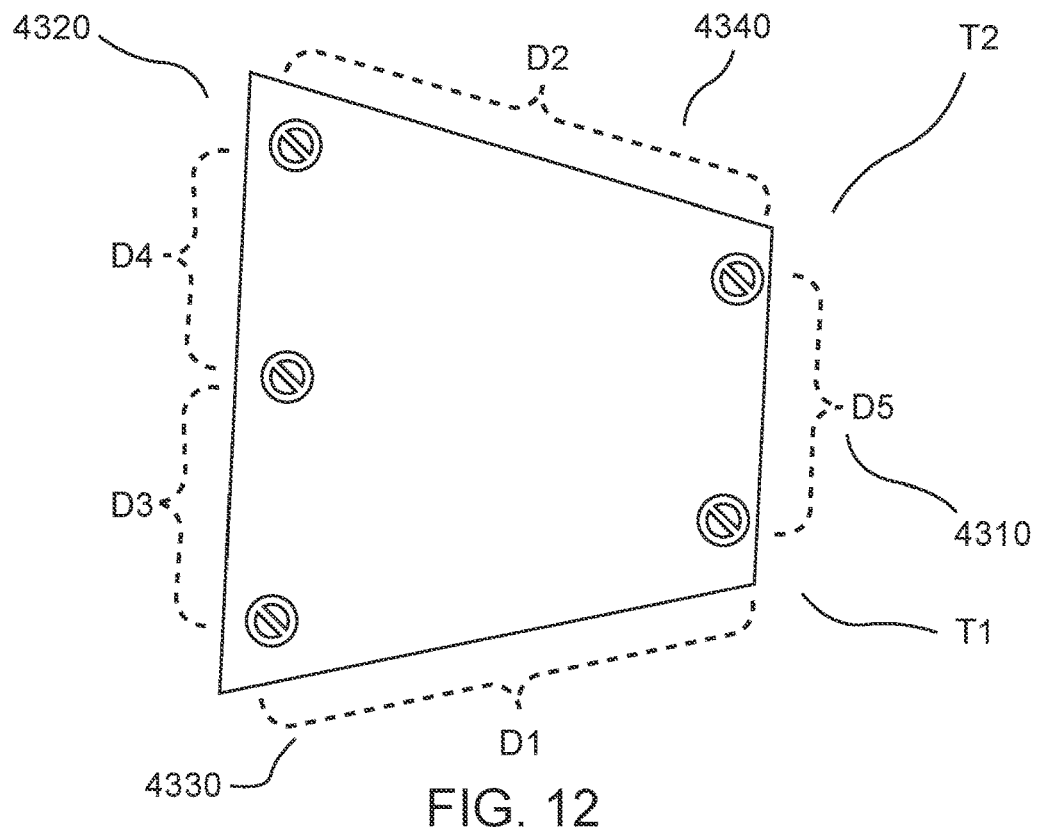
FIG. 12 is a top view of an implant for the shoulder joint according to an embodiment.

In some embodiments, as shown in FIGS. 11 and 12, the method includes measuring a first distance D1 from the medial anchors to a first target location T1 of a lateral margin or edge of a graft 4300. In some embodiments, the distance D1 is a distance from the medial anchor 4100a to the first target location T1 of the lateral margin of the graft 4300 on an anterior side of the graft 4300 to be implanted. In some embodiments, the method includes measuring a second distance D2 from the medial anchors to a second target location T2 of a lateral margin or edge of a graft 4300. In some embodiments, the distance D2 is a distance from the medial anchor 4100c to the second target location T2 of the lateral margin of the graft 4300 on an anterior side of the graft 4300 to be implanted. In some embodiments, the distances D1 and D2 can be selected such that the graft 4300 extends to a lateral-most position relative to the native rotator cuff when the graft 4300 is secured by the lateral anchors (described below). In some embodiments, the measurements are taken using a ruler or other measurement device arthroscopically as will be appreciated by one skilled in the art.

In some embodiments, the method includes measuring a third distance D3 between the first medial anchor 4100a and the second medial anchor 4100b to correlate medial anchor placement with suture placement on a corresponding medial end portion 4320 of the graft 4300. In some embodiments, the method includes measuring a fourth distance D4 between the second medial anchor 4100b and the third medial anchor 4100c to correlate medial anchor placement with suture placement on a corresponding medial end portion 4320 of the graft 4300. In some embodiments, the method includes measuring a fifth distance D5 between the first target location T1 and second target location T2 to correlate lateral anchor placement and suture placement associated with a corresponding lateral end portion 4310 of the graft 4300. In some embodiments, the method includes mounting lateral anchors 4100d, 4100e at or near the first target location T1 and the second target location T2, respectively. For example, the lateral anchors 4100d, 4100e may be mounted medially about 0 mm to about 10 mm from the first and second target locations T1, T2. In some embodiments, the lateral anchors 4100*d*, 4100*e* are mounted to the greater tuberosity 114 together with or after the graft 4300 has been positioned on the proximal humerus portion 112.

In some embodiments, the method includes preparing and sizing the graft 4300 to extend up to and/or beyond the first, second, third, fourth, and fifth distances D1, D2, D3, D4, D5. In some embodiments, the graft 4300 is sized to extend about 5 mm to 10 mm beyond the measured distances to ensure that the graft 4300 is not undersized and can be appropriately secured to the one or more anchors (e.g., anchors 4100*a*, 4100*b*, 4100*c*, 4100*d*, 4100*e*). In some embodiments, the preparing and sizing of the graft 4300 may include establishing an excess cuff extending from a posterior side portion 4340 to enable suturing and fixation to infraspinatus of an intact rotator cuff. In some embodiments, the graft 4300 may include an excess cuff extending from an anterior side portion 4330 to enable suturing and fixation to the sub scapularis of an intact rotator cuff. In some embodiments, the graft 4300 is marked on a supermedial surface for orientation and identification purposes.

Figure 13:
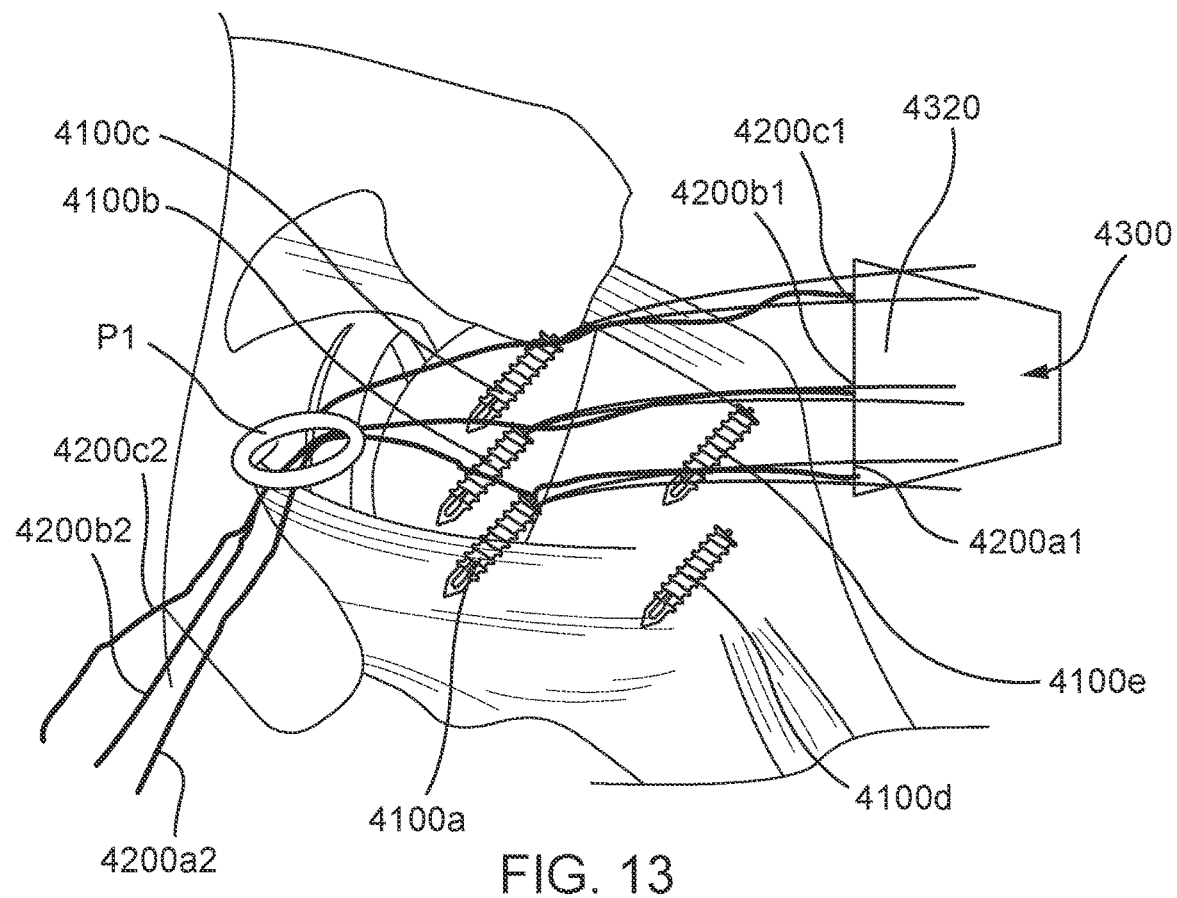
FIG. 13 is a perspective view of an implant being delivered to the shoulder joint of FIG. 10 according to an embodiment.

In some embodiments, the method includes delivering the graft 4300 to a subacromial space between the proximal humerus portion 112 and the acromion 130. As shown in FIG. 13, the method includes tying or fixing a first end of the sutures 4200*a*1, 4200*b*1, 4200*c*1 (which are secured to the medial anchors 4100*a*, 4100*b*, 4100*c*) to the medial end portion 4320 of the graft 4300. The method includes feeding a second end of one or more of the sutures 4200*a*2, 4200*b*2, 4200*c*2 from inside the patient to an external environment through a portal P1. The method further includes pulling the one or more of the second ends of the sutures 4200*a*2, 4200*b*2, 4200*c*2, which in turn pulls the graft 4300 into a desired location over the proximal humerus portion 112 by pulling the graft 4300 toward the medial anchors 4100*a*, 4100*b*, 4100*c*. In some embodiments, the medial end portion 4320 of the graft 4300 is fixed to the medial anchors 4100*a*, 4100*b*, 4100*c* using a knotless construct as will be appreciated by one skilled in the art. As shown in FIG. 13, the graft 4300 may be delivered to the desired location via open surgery.

Figure 14:
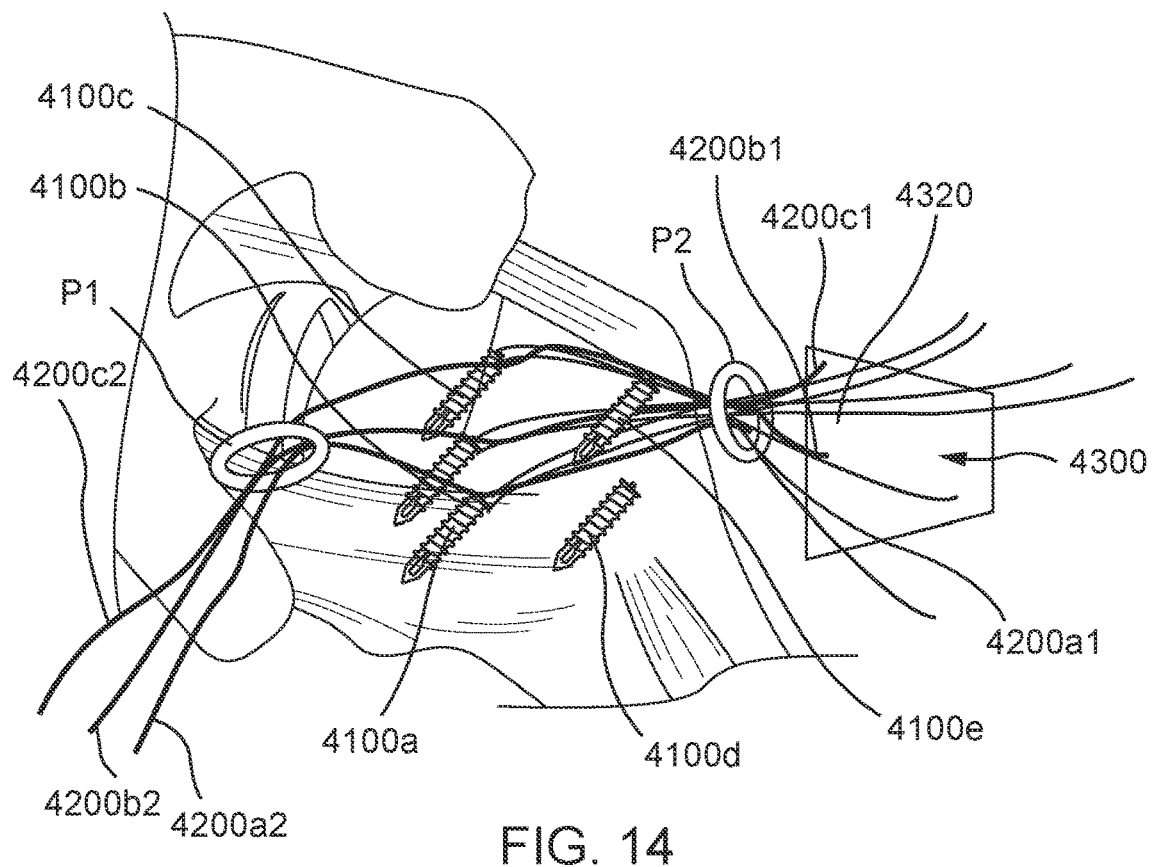
FIG. 14 is a perspective view of an implant being delivered to the shoulder joint of FIG. 10 according to an embodiment.

In some embodiments, as shown in FIG. 14, the graft 4300 may be delivered through a cannula or enlarged port P2 sized to receive a graft. Similar to FIG. 13, the method includes tying or fixing a first end of the sutures 4200*a*1, 4200*b*1, 4200*c*1 (which are passed through to the medial anchors 4100*a*, 4100*b*, 4100*c*) to the medial end portion 4320 of the graft 4300. The method includes feeding a second end of one or more of the sutures 4200*a*2, 4200*b*2, 4200*c*2 from inside the patient to an external environment through a portal P1. In some embodiments, the method further includes folding and/or rolling the graft 4300 to pass through the enlarged portal P2 and into the patient. The method further includes pulling the one or more of the second ends of the sutures 4200*a*2, 4200*b*2, 4200*c*2 out through the portal P1 to feed the graft 4300 through the enlarge portal P2. The method includes pulling the one or more of the second ends of the sutures 4200*a*2, 4200*b*2, 4200*c*2 until the medial end portion 4320 is against or over the medial anchors 4100*a*, 4100*b*, 4100*c*. In some embodiments, the method includes clamping or securing the enlarged portal P2 to the patient to assist with passage and delivery of the graft 4300 into the subacromial space.

Figure 15:
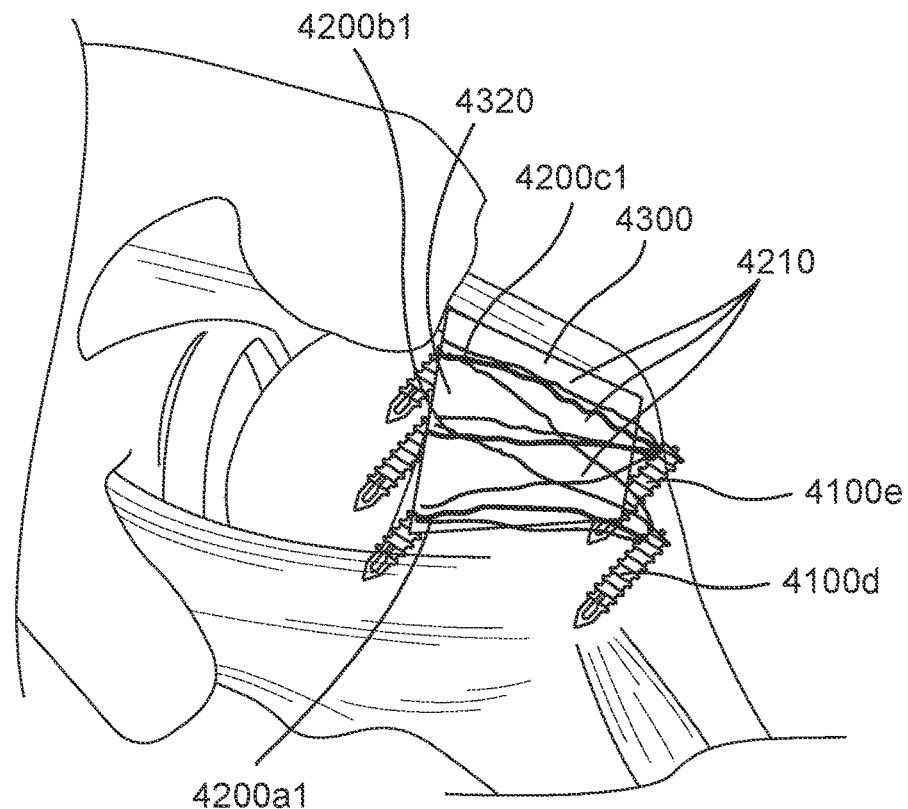
FIG. 15 is a perspective view of an implant secured to the shoulder joint of FIG. 14 according to an embodiment.

In some embodiments, the medial anchors 4100*a*2, 4100*b*2, 4100*c*2 include a second set of sutures 4210. In some embodiments, as shown in FIG. 15, after medial end portion 4320 of the graft 4300 has been position over the medial anchors 4100*a*, 4100*b*, 4100*c* and has been reduced to the desired location, the method includes passing the second set of sutures 4210 over the graft 4300, thereby compressing the graft 4300 against the proximal humerus portion 112, and fixing the second set of sutures to one or more of the lateral anchors 4100*d*, 4100*e*. It is noted that although lateral anchors 4100*d*, 4100*e* are depicted in FIGS. 13 and 14 as being mounted prior to the delivery of the graft 4300, the lateral anchors 4100*d*, 4100*e* can be mounted together with or after the delivery of the graft 4300 to the proximal humerus portion 112 as described herein.

In some embodiments, the method further includes passing the second ends of the sutures 4200*a*2, 4200*b*2, 4200*c*2 laterally back over the graft 4300 towards the lateral end portion 4310 of the graft and fixing the second ends of the sutures 4200*a*2, 4200*b*2, 4200*c*2 to one or more of the lateral anchors 4100*d*, 4100*e*. In some embodiments, the fixing of the second set of sutures 4210 and/or the second ends of the sutures 4200*a*2, 4200*b*2, 4200*c*2 is performed using a transosseous equivalent technique (TOE) where the graft 4300 is fixed to the bone by applying appropriate tension on the sutures attached to the medial end portion 4320 and then fixing the sutures to the bone (e.g., proximal humerus portion 112) and via the lateral anchors 4100*d*, 4100*e*.

Figure 16:
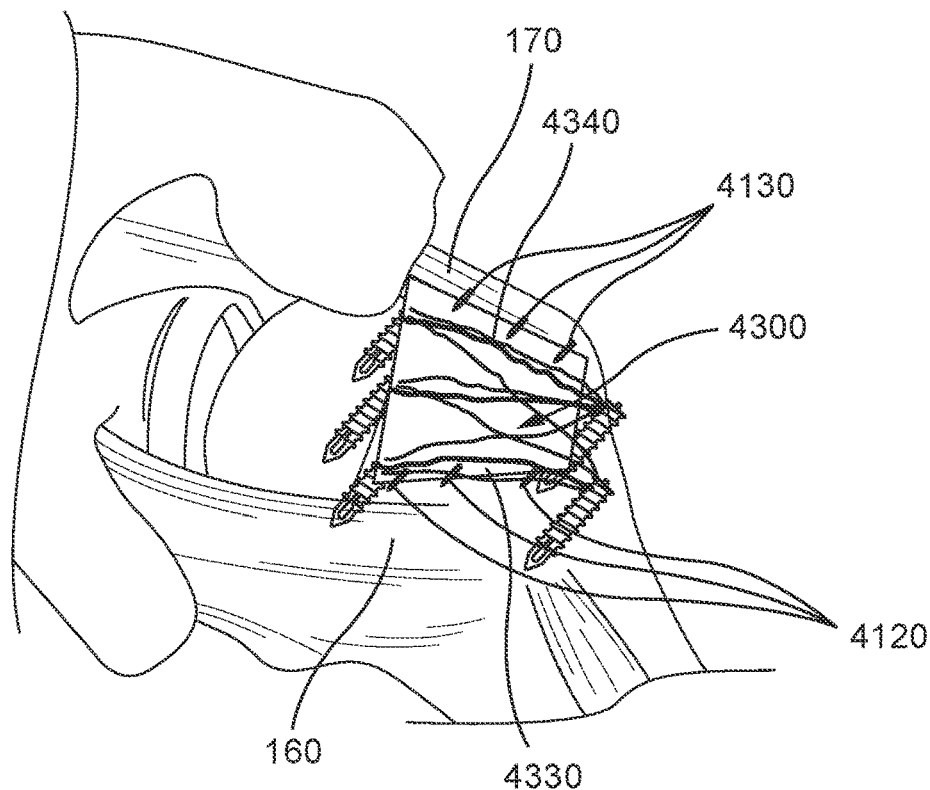
FIG. 16 is a perspective view of an implant secured to the shoulder joint of FIG. 14 according to an embodiment.

In some embodiments, as shown in FIG. 16, the graft 4300 is further secured to rotator cuff muscles. In some embodiments, the method includes securing the anterior side portion 4330 of the graft 4300 to the subscapularis muscle 160. In some embodiments, the securing to the subscapularis muscle 160 includes fixing the anterior side portion 4330 to the subscapularis muscle 160 via one or more sutures 4120. In some embodiments, method includes securing the posterior side portion 4340 of the graft 4300 to the infraspinatus muscle 170. In some embodiments, the securing to the infraspinatus muscle 170 includes fixing the posterior side portion 4340 to the infraspinatus muscle 170 via one or more sutures 4130.

Figure 17:
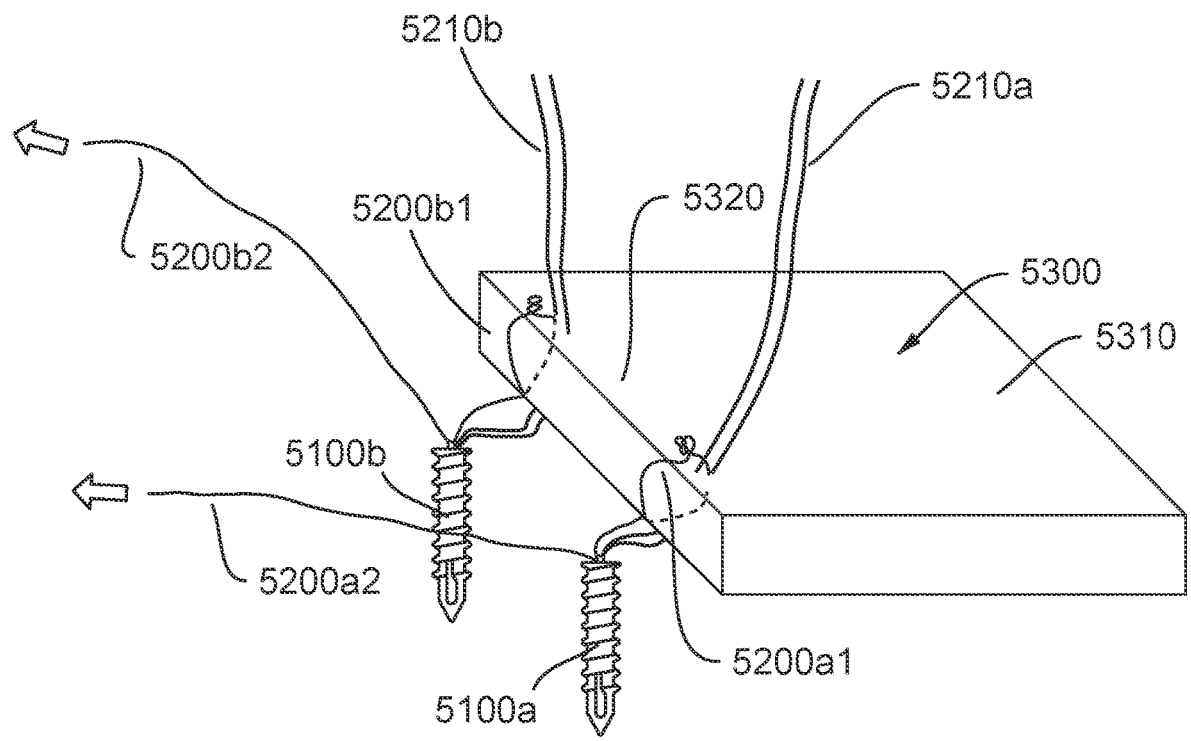
FIG. 17 is a perspective view of an implant being secured according to an embodiment.

With reference to FIG. 17, an enlarged view of a graft 5300 being secured to a medial row of anchors 5100*a*, 5100*b* is shown. Although two anchors are illustrated, it will be appreciated by one skilled in the art that the following technique can be applied to applications with two or more anchors. After the medial anchors 5100*a*, 5100*b* are secured to the humeral head 118 at a location between the tuberosity and the superior humeral head, as described by methods herein, a first end of the sutures 5200*a*1, 5200*b*1 are passed through the medial anchors 5100*a*, 5100*b* and are fixed to a medial end portion 5320 of the graft 5300. A second end of the sutures 5200*a*2, 5200*b*2 are then pulled through the medial anchors 5100*a*, 5100*b* to draw the graft 5300 into a subacromial space. In some embodiments, the second end of the sutures 5200*a*2, 5200*b*2 are pulled out to an external environment through a portal, such as an anterior portal or a posterior portal. In some embodiments, the graft 5300 is drawn into the subacromial space via open surgery. In some embodiments, the graft 5300 is drawn through a trocar or enlarged port.

Figure 18:
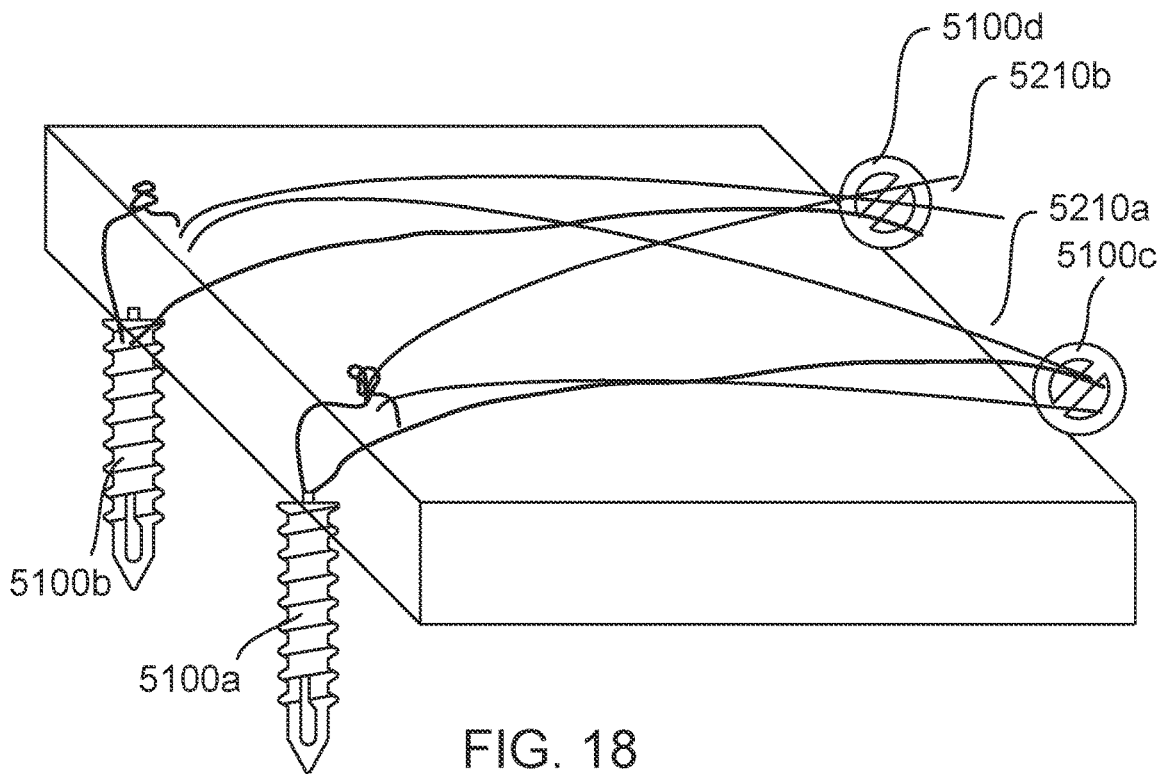
FIG. 18 is a perspective view of an implant being secured according to an embodiment.

In some embodiments, as shown in FIG. 18, once the graft 5300 has been maneuvered to a desired location over the proximal humerus portion 112, the first end of the sutures 5200*a*1, 5200*b*1 are tied to the medial end portion 5320 of the graft 5300. In some embodiments, the first end of the sutures 5200*a*1, 5200*b*1 are brought back to a lateral end portion 5310 of the graft 5300 and secured to the lateral anchors 5100*c*, 5100*d*. In some embodiments, a second set of sutures 5210*a*, 5210*b* secured to the medial anchors

5100*a*, 5100*b* are maneuvered laterally over the graft 5300 and secured to the lateral anchors 5100*c*, 5100*d* such that the second set of sutures 5210*a*, 5210*b* compress the graft 5300. In some embodiments, both the first end of the sutures 5200*a*1, 5200*b*1 and the second set of sutures 5210*a*, 5210*b* are configured to compress the graft 5300. It will be appreciated by one skilled in the art the method of securing the graft 5300 to the proximal humerus portion 112 using knotless suture techniques or alternative anchoring methods.

Figure 19:
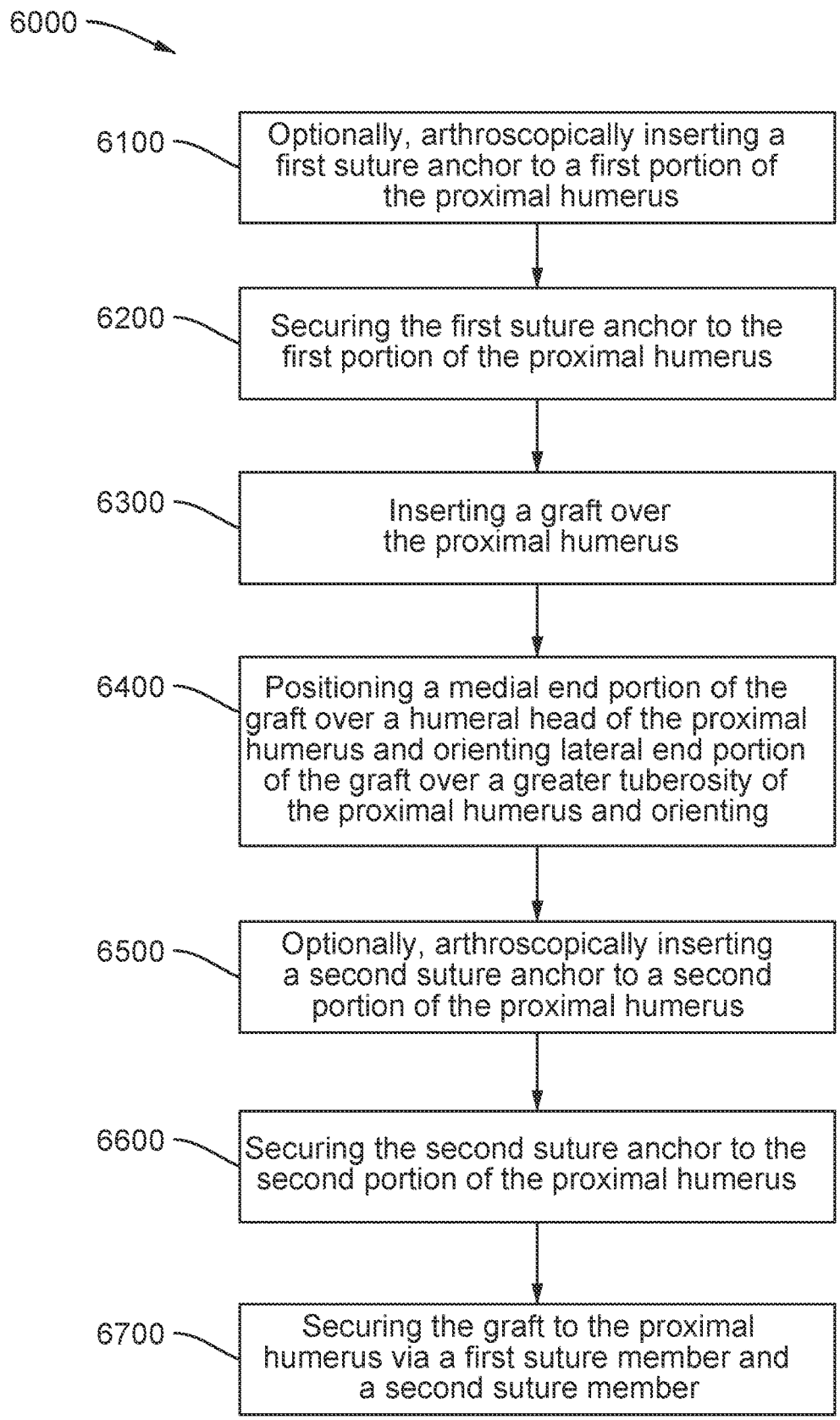
FIG. 19 is a flow chart showing a method of implanting a graft in a patient according to an embodiment.

FIG. 19 is a flow chart showing a method 6000 of performing shoulder joint reconstruction including implantation of a graft onto a proximal humerus. The method 6000 includes optionally arthroscopically inserting at 6100 a first suture anchor to a first portion of the proximal humerus. The method 6000 includes securing at 6200 the first suture anchor to the first portion of the proximal humerus. The method 6000 includes inserting at 6300 a graft over the proximal humerus. The method 4000 further includes positioning at 6400 a medial portion of the graft over a humeral head of the proximal humerus and orienting a lateral portion of the graft over a greater tuberosity of the proximal humerus. The method 6000 includes optionally arthroscopically inserting at 6500 a second suture anchor to a second portion of the proximal humerus. The method 6000 includes securing at 6600 the second suture anchor to the second portion of the proximal humerus. The method 6000 includes securing at 6700 the graft to the proximal humerus via a first suture member and a second suture member.

Figure 20:
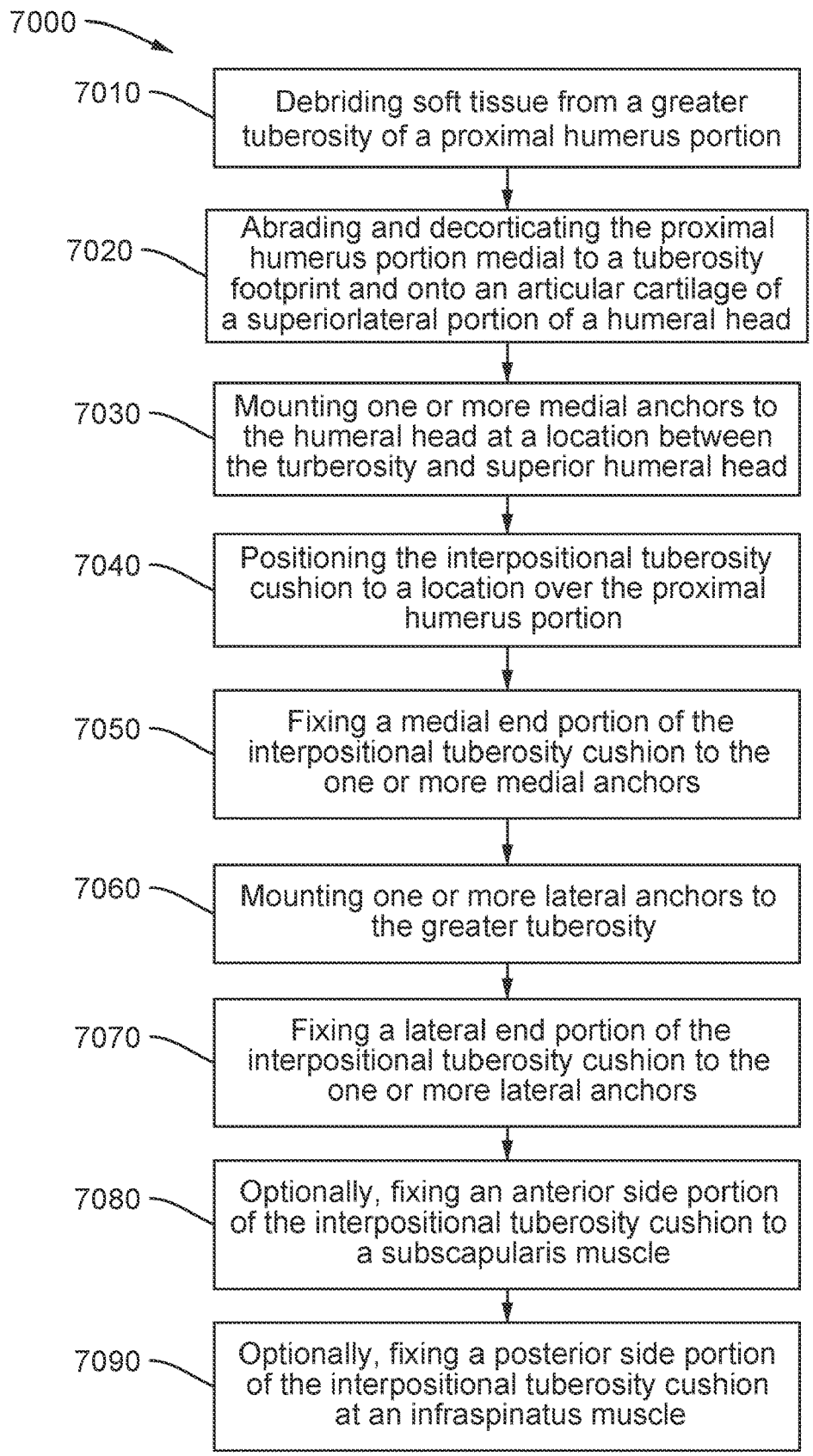
FIG. 20 is a flow chart showing a method of implanting an interpositional tuberosity cushion in a patient according to an embodiment.

FIG. 20 is a flow chart showing a method 7000 of implanting an interpositional tuberosity cushion. In some embodiments, the method 7000 includes at 7010 debriding soft tissue from a greater tuberosity of a proximal humerus portion. In some embodiments, the method 7000 includes at 7020 abrading and decorticating the proximal humerus portion medial to a tuberosity footprint and onto an articular cartilage of a superiorlateral portion of a humeral head. In some embodiments, the method 7000 includes at 7030 mounting one or more medial anchors to the humeral head at a location between the tuberosity and superior humeral head. In some embodiments, the method 7000 includes at 7040 positioning the interpositional tuberosity cushion to a location over the proximal humerus portion. In some embodiments, the method 7000 includes at 7050 fixing a medial end portion of the interpositional tuberosity cushion to the one or more medial anchors. In some embodiments, the method 7000 includes at 7060 mounting one or more lateral anchors to the greater tuberosity. In some embodiments, the method 7000 includes at 7070 fixing a lateral end portion of the interpositional tuberosity cushion to the one or more lateral anchors. In some embodiments, the method 7000 optionally includes at 7080 fixing an anterior side portion of the interpositional tuberosity cushion to a subscapularis muscle. In some embodiments, the method 7000 optionally includes at 7090 fixing a posterior side portion of the interpositional tuberosity cushion at an infraspinatus muscle. In some embodiments, the interpositional tuberosity cushion is a biologic or non-biologic graft. In some embodiments, the biologic grafts is an allograft selected from one or more of a quadricep tendon, an achilles tendon, or gluteus medius tendon. In some embodiments, the biologic allograft may be a single or multi-layered dermis or fascia lata. In some embodiments, the non-biologic (or synthetic) graft is constructed from silicon (e.g., a silicon implant).

The methods 6000 and 7000 described above and the methods described herein include securing the graft directly to the surface of the humerus, and not as a patch or other therapeutic implant that is placed onto the tendons and soft tissue of the rotator cuff above the bone surface to facilitate healing of such soft tissue. Rather, as described above, the methods of placement described herein produce a graft that is secured to and moves with the humerus to reduce pain and improve joint mobility. Thus, in some embodiments, the method may include resurfacing, debriding, or otherwise preparing the surface of the greater tuberosity or other portions of the proximal humerus prior to the positioning of the graft.

Any of the implants or kits described herein can include any suitable suture anchor. For example, any of the anchors described herein can be a knotless suture anchor that includes (or is attached to) one or more sutures. In some embodiments, any of the anchors described herein can include (or be attached to) sutures and/or tapes. Thus, where the methods described herein refer securing a graft to a proximal humerus by tensioning one or more sutures, in other embodiments, any of the methods described herein can include securing a graft to a proximal humerus by tensioning one or more tapes, fibrous members, or other flexible mechanisms for securing the graft to the proximal humerus.

As described herein, the implants and methods for shoulder joint reconstruction fixes a graft to the proximal humerus and the graft may be sized to cover the greater tuberosity and even the superior aspect of the humeral head. By securing the graft to only the proximal humerus, the graft remains detached from the glenoid and the acromion. The implant and methods described herein provide a tensionless repair to the bone and attenuates pulling forces which may prevent or delay healing in the area. The tensionless repair also enables healing of the intact anterior and/or posterior rotator cuff to the implant. Additionally, by securing the graft to the proximal humerus, the graft is not left free floating, which could lead to unintended migration or shifting. To further promote healing to the proximal humerus, the method may further include a resurfacing procedure, such as resurfacing of the greater tuberosity prior to attachment of the graft. In some embodiments, the resurfacing includes arthroscopic tuberoplasty.

Furthermore, the positioning of the implant serves to cushion the interface between the proximal humerus and the underside of the acromion where the natural cushioning and buffer may be reduced or lost from an irreparable rotator cuff tear. Basically serving as an interpositional cushioning device or implant.

Kinematics may also be improved by an implant by increasing the acromial-humeral distance and thus pushing the humeral head lower into a more optimal kinematic position.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made. Additionally, while the implants and methods described herein provide an improved option for patients with "irreparable" rotator cuffs, the implants and methods of the present disclosure can also be used in conjunction with other rotator cuff repairs.

For example, although procedures and implant systems described herein employ sutures to secure the graft to the proximal humerus, in other embodiments, a graft can be secured to the proximal humerus without sutures. For example, in some embodiments, the graft can be constructed from a synthetic material, such as, silicon. In such embodiments, the graft can be secured to the humerus using only anchors or screws into the humerus. In yet other embodiments, a graft can be secured to the humerus via bone cement or other adhesive.

In some embodiments, an implant system (or kit) includes a graft that is shaped (or configured to be shaped) to cover the proximal humerus (including the greater tuberosity and the even superior aspect of the humeral head). The graft can have any suitable thickness as described herein and can function to cushion the interface between the proximal humerus and the underside of the acromion. Thus, the graft (when placed according to the methods described herein) acts as an interpositional "pillow" between the two bones which often articulate in the setting of an irreparable rotator cuff tear.

Any of the methods described herein can be performed arthroscopically or open depending on the discretion and comfort of the surgeon.

Although various embodiments have been described as having particular features and/or combinations of components, other embodiments are possible having a combination of any features and/or components from any of embodiments as discussed above. Aspects have been described in the general context of shoulder joint reconstruction, but inventive aspects are not necessarily limited to use in the shoulder joint.

What is claimed is:

1. A method of implanting an interpositional graft onto a proximal humerus of a patient having an irreparable rotator cuff tear, the method comprising:
   placing one or more medial anchors into a humeral head at a first location medial to a greater tuberosity of the proximal humerus;
   placing one or more lateral anchors within the greater tuberosity of the proximal humerus;
   positioning the interpositional graft about at least a portion of the greater tuberosity;
   fixing a medial end portion of the interpositional graft to the one or more medial anchors; and
   fixing a lateral end portion of the interpositional graft to the one or more lateral anchors,
   wherein the interpositional graft is secured only to the proximal humerus.

2. The method of claim 1, further comprising:
   debriding soft tissue from the greater tuberosity of the proximal humerus.

3. The method of claim 1, further comprising:
   decorticating, before positioning the interpositional graft, a portion of the proximal humerus.

4. The method of claim 3, further comprising:
   the portion of the proximal humerus is medial to a tuberosity footprint and onto an articular cartilage of a superiorlateral portion of the humeral head.

5. The method of claim 1, wherein the interpositional graft is a biologic graft.

6. The method of claim 1, wherein the first location is between the greater tuberosity and a superior humeral head.

7. The method of claim 1, wherein:
   the fixing the medial end portion of the interpositional graft includes tensioning a suture or a tape coupled to the one or more medial anchors.

8. The method of claim 1, wherein after being secured, the interpositional graft does not produce any tension on the proximal humerus.

9. The method of claim 1, wherein the interpositional graft is a single-layer dermal graft.

10. A method of implanting a graft onto a proximal humerus of a patient having an irreparable rotator cuff tear, comprising:
    securing a first suture anchor to a first portion of the proximal humerus, the first suture anchor including a first suture member;
    securing a second suture anchor to a second portion of the proximal humerus, the second suture anchor including a second suture member;
    inserting the graft over the proximal humerus, the graft having a lateral portion and a medial portion;
    positioning the graft about the proximal humerus, the positioning including orienting the lateral portion of the graft over a greater tuberosity of the proximal humerus and orienting the medial portion of the graft over a humeral head of the proximal humerus; and
    securing the graft to the proximal humerus by tensioning the first suture member and the second suture member,
    wherein the graft is secured only to the proximal humerus.

11. The method of claim 10, wherein the positioning the graft includes orienting the medial portion of the graft over a superior portion of the humeral head.

12. The method of claim 11, wherein the securing includes securing the lateral portion of the graft to the greater tuberosity and securing the medial portion of the graft to the superior portion of the humeral head.

13. The method of claim 10, wherein:
    the securing the first suture anchor includes inserting the first suture anchor into the humeral head of the proximal humerus; and
    the securing the second suture anchor includes inserting the second suture anchor into the greater tuberosity of the proximal humerus.

14. The method of claim 10, further comprising:
    securing a third suture anchor to a third portion of the proximal humerus, the securing the third suture anchor includes inserting the third suture anchor into the humeral head of the proximal humerus, the third suture anchor being anteriorly offset from the first suture anchor; and
    securing a fourth suture anchor to a fourth portion of the proximal humerus, the securing the fourth suture anchor includes inserting the fourth suture anchor into the greater tuberosity of the proximal humerus, the fourth suture anchor being anteriorly offset from the second suture anchor.

15. The method of claim 14, further comprising securing a fifth suture anchor to the proximal humerus, the securing the fifth suture anchor includes inserting the fifth suture anchor into the humeral head of the proximal humerus, the fifth suture anchor being anteriorly offset from the third suture anchor.

16. The method of claim 10, further comprising resurfacing at least one of the humeral head or the greater tuberosity of the proximal humerus prior to the positioning of the graft.

17. The method of claim 16, wherein the resurfacing includes at least one of debriding soft tissue, decorticating a portion of the humeral head or the greater tuberosity, or performing arthroscopic tuberoplasty.

18. The method of claim 10, wherein the first suture anchor includes any of a knotless anchor or a screw portion.

19. The method of claim 10, wherein the graft has a thickness of between about 3 mm to 8 mm.

20. The method of claim 10, wherein after being secured the graft moves together with the proximal humerus and independent of an acromion of the patient.

21. The method of claim 10, wherein after being secured the graft moves together with the proximal humerus and independent of a glenoid of the patient.

* * * * *